US008301387B2

(12) United States Patent
Hwa et al.

(10) Patent No.: US 8,301,387 B2
(45) Date of Patent: Oct. 30, 2012

(54) COMBINATORIAL TRANSCRIPTION CONTROL FOR PROGRAMMED GENETIC RESPONSE

(75) Inventors: Terence Tai-Li Hwa, La Jolla, CA (US); Ulrich Gerland, Munich (DE); Nicolas Buchler, New York, NY (US)

(73) Assignee: The Regents of the University of California, Oakland, CA (US)

( * ) Notice: Subject to any disclaimer, the term of this patent is extended or adjusted under 35 U.S.C. 154(b) by 1702 days.

(21) Appl. No.: 10/537,950

(22) PCT Filed: Dec. 9, 2003

(86) PCT No.: PCT/US03/38995
§ 371 (c)(1),
(2), (4) Date: Jun. 8, 2005

(87) PCT Pub. No.: WO2004/053088
PCT Pub. Date: Jun. 24, 2004

(65) Prior Publication Data
US 2006/0051838 A1 Mar. 9, 2006

Related U.S. Application Data

(60) Provisional application No. 60/431,904, filed on Dec. 9, 2002.

(51) Int. Cl.
*G01N 33/48* (2006.01)
*G01N 33/50* (2006.01)
*G01N 31/00* (2006.01)
*C12Q 1/68* (2006.01)

(52) U.S. Cl. ............... 702/19; 702/20; 702/22; 435/6.1
(58) Field of Classification Search ...................... None
See application file for complete search history.

(56) References Cited

U.S. PATENT DOCUMENTS

| 5,535,382 A | * | 7/1996 | Ogawa ............................. 707/5 |
| 5,717,058 A | * | 2/1998 | Matthews et al. ............. 530/328 |
| 5,814,618 A | | 9/1998 | Bujard et al. |
| 5,834,236 A | | 11/1998 | Lamb et al. |
| 5,879,917 A | * | 3/1999 | Essigmann et al. ........... 435/440 |

(Continued)

FOREIGN PATENT DOCUMENTS
WO WO 94/12015 6/1994

OTHER PUBLICATIONS

Kirch et al. Expression of human p53 requires synergistic activation of transcription from the p53 promoter by AP-1, NF-kappaB, and Myc/Max. Oncogene, vol. 18, pp. 2728-2738, 1999.*

(Continued)

*Primary Examiner* — Russell S Negin
(74) *Attorney, Agent, or Firm* — Eleanor M. Musick; Procopio, Cory, Hargreaves & Savitch LLP

(57) ABSTRACT

A scheme is provided for selecting the regulatory DNA sequences to exert combinatorial control of gene transcription in vivo by multiple regulatory proteins, i.e., transcription factors (TFs). The method provides the ability to implement a wide range of complex logic functions through the manipulation of the regulatory DNA sequences, typically several hundred bases in length. The method includes procedures for selecting the strengths of the binding sites of different TFs and their relative positioning in order to implement a plurality of different logic functions.

36 Claims, 9 Drawing Sheets

U.S. PATENT DOCUMENTS 5,942,433 A    8/1999    Vinson et al.
5,968,773 A    10/1999   Heddle et al.

OTHER PUBLICATIONS

Gardner et al. Construction of a genetic toggle switch in *Escherichia coli*. Nature, vol. 403, Jan. 2000, pp. 339-342.*

Renkawitz R. Transcriptional repression in eukaryotes. Trends in Genetics. 1990, vol. 6, pp. 192-196.*

Orkin SH. Globin gene regulation and switching: Circa 1990. Cell. vol. 63, 1990, pp. 665-672.*

Kirchhamer et al. Modular cis-regulatory organization of developmentally expressed genes: Two genes transcribed territorially in the sea urchin embryo, and additional examples. PNAS, 1996, pp. 9322-9328.*

Wasiewicz et al. The infernce based on molecular computing. Cybernetics and Systems: An International Journal, vol. 31, pp. 283-315 (version submitted is numbered from pp. 1-27).*

Ross et al. Genetic analysis of transcription activation and repression in the Tn21 mer operon. Journal of Bacteriology, 1989, vol. 171, pp. 4009-4018.*

Cho et al. Allosteric interactions between capping enzyme subunits and the RNA polymerase II carboxy-terminal domain. Genes & Development. 1998, vol. 12, pp. 3482-3487.*

Definition of "fusion protein." (2001) Obtained online from biotechterms.org on Jul. 16, 2009. 2 pages.*

Buchler, N., et al. "On schemes of combinatorial transcription logic" *PNAS* (Apr. 29, 2003) vol. 100, pp. 5136-5141.

Gerland, U., et al., "On the Selection and Evolution of Regulatory DNA Motifs" *J. Mol. Evol.* (2002) 55:386-400.

Gerland, U., et al., "Physical constraints and functional characteristics of transcription factor—DNA interaction", *PNAS* (Sep. 17, 2002) vol. 99, pp. 12015-12020.

Ptashne, Mark, *A Genetic Switch*, Third Edition, 2004, Cold Spring Harbor Laboratory Press, pp. 1-65.

Ptashne, M. & Gann, A.; "Transcriptional activation by recruitment", Apr. 1997, *Nature*, vol. 386, pp. 569-577.

* cited by examiner

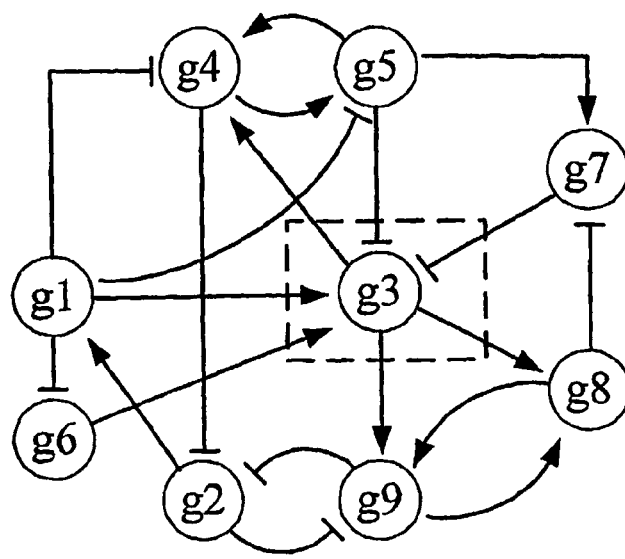
Fig. 1a
| A | B | $g_1$ | $g_2$ | $g_3$ | $g_4$ | $g_5$ | $g_6$ |
|---|---|---|---|---|---|---|---|
| low | low | OFF | OFF | OFF | ON | OFF | ON |
| high | low | OFF | OFF | ON | ON | ON | OFF |
| low | high | ON | OFF | ON | ON | ON | OFF |
| high | high | OFF | ON | ON | OFF | OFF | ON |
Fig. 1b
B AND A
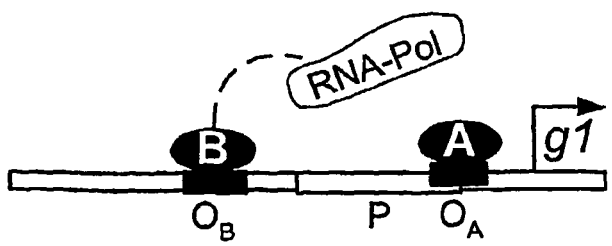
Fig. 1c

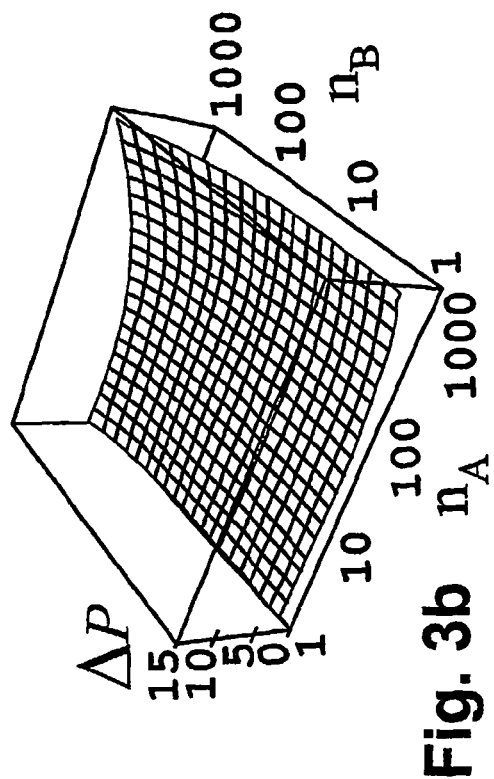
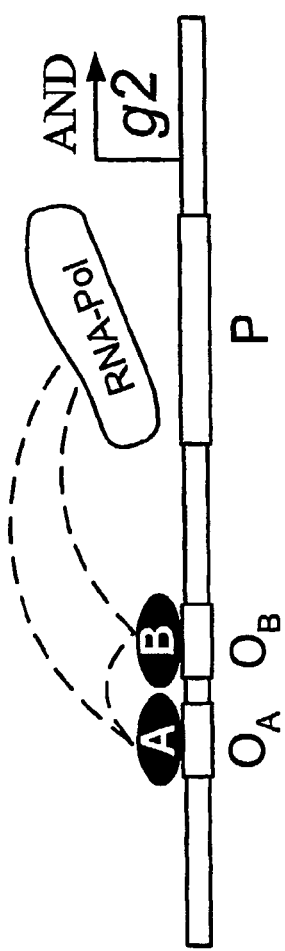
Fig. 3a
Fig. 3b (A OR B) AND (A AND B)

(B AND Ā) OR (A AND B̄)

COMBINATORIAL TRANSCRIPTION CONTROL FOR PROGRAMMED GENETIC RESPONSE

RELATED APPLICATIONS

This application claims the benefit of priority of U.S. Provisional Application Ser. No. 60/431,904 filed Dec. 9, 2002, the disclosure of which is incorporated herein by reference in its entirety.

GOVERNMENT RIGHTS

Pursuant to 35 U.S.C. §202(c), it is hereby acknowledged that the U.S. Government has certain rights in the invention described herein, which was made in part with funds from the National Science Foundation, Grants No. 9971456, No. 0083704, and No. 0211308.

BACKGROUND OF THE INVENTION

With rapidly growing databases of genome, transcriptome, and proteome sequence data, an outstanding challenge of post-genome biology is to map and understand the function of the underlying biological networks formed by an organism's genes. At the heart of these biological networks is the process of gene regulation. In general, gene regulation can involve control in the dynamics of transcription, splicing, transportation, translation, modification, and degradation of gene products.

The survival and well-being of a cell depends heavily on its ability to regulate the activities of its genes in response to changing environment and internal needs. Achieving the appropriate genetic responses requires the integration of vastly different sources of signals, e.g., availability of various nutrients, presence of hazardous chemicals, metabolic state of the cell, etc. The process of signal integration is carried out through the interactions of the signal carriers, regulatory proteins, with each other, and with DNA sequences in regulatory regions located in the vicinity of each gene. The regulatory program each gene executes is coded into the genome through the structures and chemical properties of the regulatory proteins and the composition and location of the regulatory DNA sequences.

The low level of knowledge of quantitative biochemical details and the mathematical difficulties of accurately describing these complex networks has led to the development of simple models aimed at learning general principles. This approach is based on the belief that some fundamental principles of regulation are typical properties of the systems, robust to theoretical idealization, such that they can be expressed in terms of a simplifying model. One such model is the Boolean genetic networks, which were first proposed in 1969 by Kauffman, in which an element, or "node", of the network represents a gene or a protein and can take only two values: ON (1) or OFF (0). Each node of the Boolean network is assumed to be described by a logic function that transforms a set of inputs to an output. The output is then sent to a number of other nodes through a set of pre-defined connections, i.e., "wiring", defined by the specificity of the interactions encoded in the molecular structure of the element. Such Boolean networks have been widely used to model gene networks. However, these models do not address how the specific logic functions can be implemented. Also, the binary inputs and outputs assumed in the Boolean network model are unrealistic approximations of the continuous protein concentrations or gene expression levels in a cell.

The theoretical prediction of mRNA expression patterns, beginning with the regulatory sequences, is a formidable task and will likely remain an unsolved problem in the near future. One of the obstacles to prediction is the fact that the relevant binding sites for TFs are difficult to identify using standard bioinformatics tools. Given these binding sites, a much larger obstacle still lies in the need to accurately describe the mutual interactions between RNA polymerase, TFs, and DNA.

It is well known that extensive use of cis-regulatory transcription control is made, for example, in many developmental genes of higher eukaryotic organisms, which are typically regulated by 5 to 8 different TFs (Arnone and Davidson 1997). Within the cis-regulatory region of such a gene, internal and external signals encoded in concentrations of active TFs are directly processed on the DNA through protein-protein interactions among the TFs and the RNA polymerase to determine the resulting expression level. In general, this process, called "signal integration", takes place at every "node" of a genetic network.

Gene networks are unlike an electrical network such as an integrated circuit, which processes information through synchronized cascades of a large number of simple nodes (millions to billions of transistors), and for which connectivity is the main source of network complexity. A gene network typically consists of only a few tens to hundreds of nodes, which are the regulatory genes in the genome. These nodes are slow and asynchronous, yet are sophisticated in their capacity to integrate signals: Each node can be regulated combinatorially, often by 4-5 other nodes, and the regulatory effect of one node on another can either be activating or repressive depending on the context. Combinatorial control is an important feature of regulatory networks, allowing different combinations of TFs, taken from the same larger set, to act in concert at different genes. The same combination can even implement very different functions.

Out of several different known mechanisms for gene regulation, transcription control by regulated recruitment appears to be the most flexible and general mechanism (Ptashne and Gann 1997, 1998, 2002), and it naturally allows for signal integration and combinatorial control. Regulated recruitment refers to a situation where TFs regulate transcription simply by "recruiting", i.e., attracting, RNA polymerase to the promoter sequences on the DNA. This mechanism involves only simple and generic, "glue-like" protein-protein interactions, in contrast to other known mechanisms of activation which require specific contacts to induce allosteric transitions in the conformation of the molecules. Due to the simplicity of the interactions involved in recruitment, this mechanism is particularly flexible with respect to the choice of interaction partners, which facilitates combinatorial control of gene expression.

A simple theoretical model for gene regulation in prokaryotes, which was introduced by Shea and Ackers (1985), is based on the mechanism of gene activation by recruitment and a competitive binding mechanism for repression. However, with increasing complexity of the logical functions, some general difficulties for the design process arise. The existing art, known as synthetic genetic circuits, requires the expression of multiple genes and performs computation by "cascading" their results, leading to increasingly complex logical functions. Accordingly, the need remains for a method for modeling gene regulation which does not involve the complexities of cascading.

BRIEF SUMMARY OF THE INVENTION

The present invention avoids the drawbacks of the prior art models by providing schemes for implementing the specific logic functions assumed in the Boolean network while treating protein concentrations and gene expression more realistic continuous variables.

In an exemplary embodiment, the invention provides a system and method for selecting the regulatory DNA sequences to exert combinatorial control of the transcription of target genes in vivo by multiple regulatory proteins in a modular fashion by constructing a relational model of combinatorial control of transcription by a plurality of regulatory proteins with contact and long-distance interactions, setting rules to determine a plurality of necessary interactions among the regulatory proteins and their DNA binding sites in order to implement desired logic functions, and designing a plurality of cis-regulatory DNA sequences to realize the plurality of necessary interactions by selecting the relative binding strengths and arranging the relative locations of individual DNA binding sites of the relevant regulatory proteins within a cis-regulatory region.

The present invention integrates multiple signals directly in the regulatory region without the need for additional genes and their expressions, thus avoiding the requirements of the expression of multiple genes and performing computation by "cascading" their results. The inventive method is, therefore, easier to synthesize, more robust to stochastic fluctuations associated with each stage of gene expression, and responds much faster. Further, the inventive method is modular so that the same design units can be used for different genes.

The present invention provides a scheme to select the regulatory DNA sequences to exert combinatorial control of gene transcription in vivo by multiple regulatory proteins, i.e., transcription factors (TFs). The method provides the ability to implement a wide range of complex logic functions through the manipulation of the regulatory DNA sequences, typically several hundred bases in length. The method includes procedures for selecting the strengths of the binding sites of different TFs and their relative positioning in order to implement a plurality of different logic functions.

In another aspect, the invention provides a method for controlling the transcription of target genes comprising: identifying at least one logic function having an output corresponding to a desired target gene output signal; and implementing the at least one logic function by producing interactions among a plurality of regulatory proteins and interactive binding of two or more regulatory proteins at corresponding binding sites of the target genes, where the target genes each comprise one or more cis-regulatory sequences having individual DNA binding sites, and where each binding site has a binding strength and a binding location which are adjustable by varying composition of the one or more cis-regulatory sequences; where the interactions include contact and long-distance interactions.

Yet another aspect of the invention provides a method for genetic computing using combinatorial transcription control for controlling gene expression, comprising: identifying at least one logic function having an output corresponding to a desired gene expression; and implementing the at least one logic function by producing interactions among a plurality of transcription factors and interactive binding of two or more transcription factors at corresponding binding sites of one or more target genes, where the target genes each comprise one or more cis-regulatory sequences having individual DNA binding sites, and where each binding site has a binding strength and a binding location which are adjustable by varying composition of the one or more cis-regulatory sequences.

BRIEF DESCRIPTION OF THE DRAWINGS

The invention, both as to its organization and manner of operation may be further understood by reference to the following description taken in conjunction with the following drawings wherein:

FIG. 1a is a schematic diagram representing the interconnections of a genetic network, FIG. 1b is a table providing exemplary gene responses according to activation patterns of two transcription factors, and FIG. 1c is a diagrammatic representation of a cis-regulatory implementation of the response for gene g1 in the table of FIG. 1b;

FIG. 2b is a 3-dimensional plot of the change in promoter occupancy $\Delta P(n_A, n_B)$ for the OR-gate of FIG. 2a;

FIG. 3a is a schematic diagram showing the placement of two TF binding sites with respect to the promoter in a simple representation of an AND-gate; FIG. 3b is a 3-dimensional plot of the change in promoter occupancy $\Delta P(n_A, n_B)$ for the AND-gate of FIG. 3a;

FIG. 4a is a schematic diagram showing the placement of two TF binding sites with respect to the promoter in a simple representation of a NAND-gate; FIG. 4b is a 3-dimensional plot of the change in promoter occupancy for the NAND-gate of FIG. 4a;

FIG. 5b is a 3-dimensional plot of the change in promoter occupancy $\Delta P(n_A, n_B)$ for the XOR-gate of FIG. 5a.

FIG. 9b is a 3-dimensional plot of the change in promoter occupancy $\Delta P(n_A, n_B)$ for the EQ-gate of FIG. 9a.

DETAILED DESCRIPTION OF THE PREFERRED EMBODIMENTS

Figure 2B:
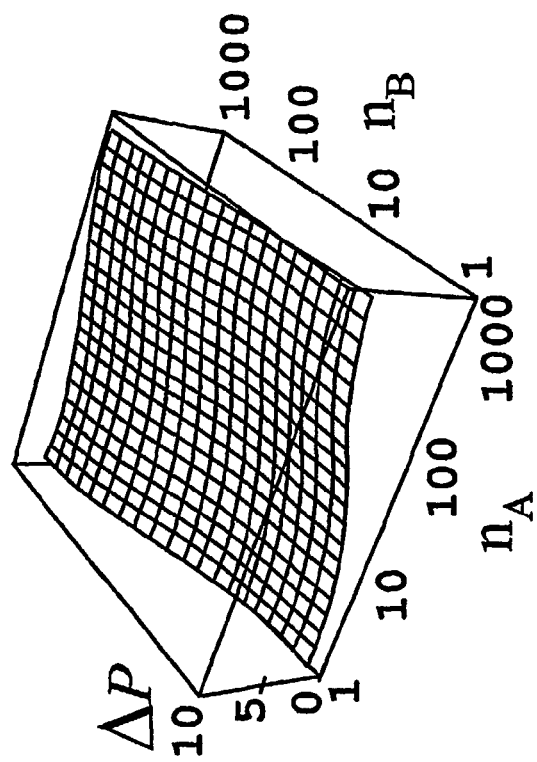

According to the present invention, a method and model are provided for the implementation of a wide class of cis-regulatory logics based only on selecting and juxtaposing binding sequences on the genomic DNA. Using an approach similar to that of Shea and Ackers (1985), the model is applied to cis-regulatory sequences that implement specified logic functions. The problem of increasingly complex logical functions can be largely overcome by incorporating a mechanism for long-distance repression, which is experimentally well documented in eukaryotes (Courey and Jia 2001).

Genetic networks are frequently represented graphically as shown in FIG. 1a. In the figure, the "wiring" of the network is indicated by lines connecting the genes, i.e., the "nodes" of the network, and arrows or bars at the end of lines denote a stimulating or inhibitory effect on gene expression, respectively. The activity of a node is regulated by other nodes through the concentrations of their gene products, which is accomplished mechanically by the interaction of TFs with their respective DNA targets, with each other, and with the RNA polymerase complex (RNAP) in the regulatory region of the regulated gene. Regulation can be quantified by the "response characteristics", i.e., the degree of gene expression for each combination of (activated) TF concentrations in an activated state which allows specific DNA binding and affects the expression of the regulated gene. Activation of TFs can be controlled by a number of mechanisms such as phosphorylation and ligand binding. Essential features of the response characteristics can often be represented more compactly by a binary "logic function", which specifies whether a gene is ON (expressed) or OFF (silent, or expressed at basal level) at different extremes of cellular TF concentrations ("high" or "low").

For purposes of the description of the inventive method, focus is directed toward an isolated node, which can be viewed, for example, as information processing unit g in FIG. 1a. Inputs to the cis-regulatory region of the gene are the concentrations of (one or several) TFs, while the outputs consist of an expression level. The input concentrations may be the direct output of another gene, or they may be additionally regulated through external or internal signals, e.g., a ligand which induces an allosteric transition in the TF from a non-DNA-binding to a DNA-binding form. As part of a larger composite network, the node can display a complex dynamic behavior, however, for purposes of the description, focus is directed to the static input-output characteristics of the node. To provide an explicit model, a number of simple assumptions can be made with regard to the molecular interactions in the regulatory region, which are described in the following discussion.

Protein-DNA binding: A simple modular structure can be assumed for the TFs with several distinct functional domains for DNA-binding and protein-protein interactions (Frankel and Kim 1991). Interactions among the TFs, the DNA, and the RNA polymerase are treated as simple pairwise interactions, not invoking any allosteric effects (apart from possible TF activation by ligand binding). The binding affinity of a TF to a particular operator sequence on the DNA can be expressed through its binding threshold n, i.e., the factor concentration n at which the probability of occupancy $P_0$ becomes 50%. In thermodynamic equilibrium, and without any additional protein-protein interactions, $P_0$ takes the Arrhenius (or Fermi function) form. (See, e.g. von Hippel and Berg (1986).)

$$p_0 = \frac{n}{n+\tilde{n}} = \frac{q}{1+q}. \quad (1)$$

(The relative weight of binding $q=n/\tilde{n}$ is introduced for convenience in a later discussion.) In general, the binding threshold n depends on (i) how closely the operator sequence matches the best binding nucleotide sequence (which is specific to the particular TF), (ii) the protein-DNA interaction parameters of that TF, and (iii) the rest of the genomic sequence (von Hippel and Berg 1986; Stormo and Fields 1998). A recent theoretical study (Gerland et al. 2002) indicates that the typical protein-DNA interaction parameters of prokaryotic TFs allow almost maximal programmability of the binding threshold n over the full range of typical cellular TF concentrations, e.g., from 1 to 1000 molecules per cell or higher, through the choice of the operator sequence alone. Within the proposed model, this appears to be true for all TFs. RNA polymerase-DNA interaction can be treated in the same way.

TF-TF interactions: Cooperative protein-DNA binding is the biophysical basis for gene regulation by regulated recruitment. A cooperative interaction between DNA-bound proteins A and B lowers the binding threshold of their binding sites, i.e., effectively increases their local concentrations. The cooperativity $\omega_{AB}$ is defined as the ratio of the Boltzmann weights for simultaneous binding over independent binding, i.e., $\omega_{AB} \equiv q_{AB}/q_A q_B$. In the present model, the cooperativity between two TFs is entirely determined through the relative placement of their binding sequences. Coooperativity can be assumed to take one of three values:

$$\omega_{AB} \in \{0, 1, \omega > 1\}. \quad (2)$$

The first case corresponds to a competitive binding situation, arising when the two binding sequences are too closely spaced or overlapping, while the second case corresponds to the non-interacting situation at large spacing. Cooperative binding occurs only in the third case, where a correct spacing between the operators allows the attractive protein-protein contacts. For a few exemplary cases, structures of ternary TF-TF-DNA complexes have shown that these contacts typically involve hydrophobic interactions, sometimes in combination with polar interactions (Wolberger 1999). While it is not presently known to what extent such protein-protein interactions are specific or generic promiscuous interactions, it appears that promiscuous interactions would allow tremendous flexibility for combinatorial control. The importance of combinatorial control has been demonstrated, e.g., for the eukaryotic factor Ets which can bind cooperatively with any partner from a larger group of TFs (Li et al. 2000). According to the inventive method, completely promiscuous interactions are sufficient to allow the design of a wide range of regulatory functions. To this end, $\omega$ is not treated as a programmable parameter, but is held at the same fixed value for all TF pairs. A range of $10 < \omega < 100$ appears to be reasonable given cooperative binding energies on the order of a few $k_B Ts$. (For example, the experimentally known cooperative binding energies involved in the phage lambda lysis-lysogeny switch are about $3 k_B T$, (see Shea and Ackers (1985)) and references therein.) In fact, the results are insensitive to the precise value of $\omega$.

TF-Polymerase interactions: For the large class of prokaryotic and eukaryotic TFs that work by regulated recruitment, the TF-polymerase interaction involves simple protein-protein interactions that are weak and non-specific (Ptashne and Gann 2002). Given the size of the RNA polymerase complex and the flexible structure of some of its domains, TFs can contact it in several different locations, which allows (i) a certain degree of freedom in the placement of the activating TF binding sites, and (ii) simultaneous (synergistic) interaction of multiple TFs with polymerase (Joung et al. 1994). Qualitative results do not depend on the choice between synergistic and non-synergistic interaction, so it would be preferable to assume the non-synergistic case, since it seems to require less "fine-tuning" for the positioning of the binding sites. On the other hand, this choice can make a difference for the quantitative characteristics of some regulatory functions. For simplicity, the same cooperativity ω for TF-polymerase interaction can be assumed for TF-TF interaction. The effect of binding site placement can be included by permitting the three choices of Equation (2) for each binding site.

Gene expression level: The assembly/disassembly of the TF-DNA-polymerase complex in the cis-regulatory region can be viewed as an equilibrium process, and the rate of transcription initiation taken to be proportional to the thermodynamic occupancy of the promoter by polymerase, similar to previous models in the literature (Shea and Ackers 1985; Wolf and Eeckman 1998). At least for prokaryotes, it is well known that transcription initiation can be considered as a two step process to first approximation: RNA polymerase binding to the promoter forming a "closed complex", followed by local melting of the DNA to form the "open complex" and beginning of transcription (McClure 1980). In the common case of gene regulation by recruitment, the formation of the closed complex is the rate-limiting step. For eukaryotes, there is also evidence that the assembly of the core transcription machinery at the promoter typically takes much longer than the transition from the initiation to the elongation phase, see, e.g., Misteli (2001) and references therein. Neglecting possible gene control in the elongation phase or at the level of translation, the gene expression level is then proportional to the binding probability $P_B$ of polymerase to the promoter, which is discussed in more detail below.

The model described herein is minimal in the sense that it incorporates only tunable specific protein-DNA interactions and non-specific protein-protein interactions which can be controlled only through the placement of the binding sites. This model is not detailed in that it does not take "mechanical" properties such as DNA bending into account. Rather, the model identifies simple generic aspects of cis-regulatory transcription control. The model does not assume any mechanisms which have not been documented experimentally and therefore is sufficiently realistic to permit meaningful conclusions.

Using the inventive model, the gene expression level P can be calculated using standard equilibrium statistical mechanics. Within the model, each operator sequence has an associated statistical weight, q, for occupancy by the corresponding TF alone. Assuming that the mutual sterical exclusion of the TFs bound to the rest of the genome can be neglected (Gerland et al. 2002), this weight is simply the ratio of the TF concentration n (a control variable), and the binding threshold of the operator, ñ (a programmable parameter), i.e., q=n/ñ. (This approximation can be justified by the fact that typical TF concentrations inside prokaryotic cells are very low, usually no more than a few hundred molecules, and furthermore, the protein-DNA interaction parameters are such that the dominant contribution of the genomic background comes from a large number of binding sites with relatively low affinity (Gerland et al. 2002).) The promoter-polymerase interaction is handled in the same way, except that the polymerase concentration is not a control variable and is taken as a constant. The "strength" of a particular promoter is, therefore, measured directly by its statistical weight $q_0$ for the binding of the polymerase alone, and is taken to be a "programmable" parameter.

The pairwise interactions between DNA-bound proteins is taken into account through cooperativity factors ω. Note that this treatment is correct only for the case of weak protein-protein interactions where the interaction (free) energy, $-k_B T \log \omega$, is not sufficient to associate the two proteins without DNA-binding. However, the entropy cost of localizing the two proteins together is at least $k_B \log \Gamma$, where $\Gamma \sim 10^6$ denotes the genome size in basepairs, thus falling within the realm of weak protein-protein interaction as long as $\omega \ll \Gamma$.

The probability of promoter occupation by polymerase is taken as a measure of the gene expression level $P_{p0}$. This probability can be written as $$P_{po} = \frac{Z_{ON}}{Z_{ON} + Z_{OFF}}, \quad (3)$$

where $Z_{ON}$ and $Z_{OFF}$ denote the total statistical weight of all "states" in which the promoter is occupied and unoccupied, respectively. A state of the system can be defined as an occupancy pattern of the binding sites. For example, if there are K operators that regulate a single promoter, then the system has $2^{K+1}$ states. It can be described by K+1 Boolean variables $\sigma_j \in \{0,1\}$ which denote the occupancy of site $j=\{0, 1, \ldots, K\}$, with site "0" corresponding to the promoter.

The statistical weight for each pattern of operator occupancy can be written as:

$$W[\sigma_1, \ldots, \sigma_K] = \prod_{\substack{j \neq 0}}^{K} q_j^{\sigma_j} \prod_{\substack{i,j=1 \\ i<j}}^{K} \omega_{i,j}^{\sigma_i \sigma_j}, \quad (4)$$

where $\omega_{i,k} \in \{0, 1, \omega\}$ according to the model. $Z_{OFF}$ is then simply obtained by summing over all $\sigma_j$'s with $j \neq 0$, i.e., $$Z_{OFF} = \sum_{\sigma_1, \ldots, \sigma_K} W[\sigma_1, \ldots, \sigma_K]. \quad (5)$$

The expression for $Z_{ON}$ has the general form:

$$Z_{ON} = \sum_{\sigma_1, \ldots, \sigma_K} Q[\sigma_1, \ldots, \sigma_K] \cdot W[\sigma_1, \ldots, \sigma_K], \quad (6)$$

where the quantity Q describes statistical weight due to the presence of the polymerase and its interaction with the bound TFs. As previously stated, for simplicity, only the case where the polymerase can interact cooperatively with one TF at a time is considered. In this case, the weight Q can be written as $$Q = q_0 \prod_{i \neq 0} \left[1 - \sigma_i \cdot \delta_{\omega_{0,i},0}\right] \cdot \left[1 + \omega \sum_{j \neq 0} \sigma_j \delta_{\omega_{0,j},\omega}\right] \quad (7)$$

In Equation (7), the quantity within the first brackets ensures that the promoter cannot be occupied (i.e., Q=0) if any one of the repressor sites (i.e., those with $\omega_{o,i}=0$) is occupied. The second term in the equation describes the additional weight gained by the interaction of the promoter-bound polymerase with the TFs bound to the sites with $\omega_{o,j}=\omega$). The more realistic case in which the polymerase simultaneously interacts with two bound TFs can be written in a similar way, with a more complicated form of Q. It should be noted that Equation (3) for polymerase binding can be alternatively written as $P=\langle Q \rangle/[1+\langle Q \rangle]$, where $\langle Q \rangle = Z_{ON}/Z_{OFF}$ is the statistical average of Q in Equation (7) taken with respect to the ensemble of weights in Equation (4).

Equations (3)-(6) specify the input-output characteristic for an arbitrary cis-regulatory region within the model. The input variables are the concentrations of the TFs in total M different species (with different recognition sequences). The index of the TF that is designated to bind to site k is denoted by m(k), with $1 \leq m(k) \leq M$. To express P in terms of the input concentrations, $q_k = n_{m(k)}/ñ_k$ can be substituted into Equation (4).

The model specified by Equations (4)-(7) is of the general Ising model form, which is also the basis for many neural network models (Hertz et al. 1991). If one denotes the W in term of a "Hamiltonian" $H_{TF}$, i.e., $$Z_{OFF} = \sum_{\sigma_1,\ldots,\sigma_K} e^{-H_{TF}/k_B T},$$

then this Hamiltonian takes on the standard Ising model form, $$H_{TF} = \sum_{j=1}^{K} h_j \sigma_j + \sum_{\substack{i,j=1 \\ i<j}}^{K} J_{i,j} \sigma_i \sigma_j, \quad (8)$$

where each "spin" $\sigma_j$ experiences a local field $h_j = -k_B T \ln q_j$ and interacts with a spin-coupling energy $J_{ij} = -k_B T \ln \omega_{i,j}$. Note that the input concentrations $n_{j \neq 0}$ therefore enter only through the local fields $h_{j \neq 0}$. The output is then the expectation values of $\sigma_0$, or alternatively, the expectation value of Q which is a power of the values of $\sigma_{j \neq 0}$. In the Ising language, the task is to find a suitable set of coupling energies $J_{i,j}$ (which can only take discrete values in the inventive model) to produce different desired states of $\sigma_0$ according to different patterns of the applied fields $h_{j \neq 0}$. The latter can be independently shifted at each site through the choice of ñ, the other programmable degree of freedom.

Regulatory Functions: Consider a gene whose expression is regulated by two TFs, e.g., "A" and "B". In the example of FIG. 1a, the two inputs can either both be activating, both repressing, or one activating, one repressing. Even when it is known that, for example, both are activating as in the case of g8, from the digital logic perspective, this still does not suffice to fully characterize the node, since gene expression could be significant when either one of the input levels is high (OR-logic), or significant only when both input levels are high (AND-logic). FIG. 1b provides several examples of possible responses (ON or OFF) according to the specific activation patterns of two transcription factors A and B as denoted by their cellular concentrations (high or low).

At each node of a network, typically several input signals, i.e., concentrations of (active) TFs, $n_A$, $n_B$, $n_C$, . . . , are integrated into one output signal, the promoter occupancy $P(n_A, n_B, n_C \ldots)$. Two major levels of "complexity" can be defined within the class of possible output functions P. A regulatory function is considered "simple" if P can be represented qualitatively by arrows and bars as in FIG. 1a, i.e., the sign of the effect (activating or repressing) of a single input is well-defined and independent of the other input levels. It should be noted, however, that the magnitude of the effect may strongly depend on the other inputs. Mathematically, the "simple" regulatory functions are represented by monotonous functions whose partial derivatives have constant sign. It is also important to note that many regulatory functions cannot be represented in a meaningful way by a diagram such as FIG. 1a. Consider the example of node g8, which has activating inputs from g3 and g9. These inputs may be activating when presented separately, but the effect on g8's expression may reverse to repression when both inputs are presented simultaneously. Such context dependence is known to occur in natural gene regulation. Also, context dependent gene regulation would be very useful for the design of artificial networks, e.g., with biocomputation applications in mind. Such functions, where the sign of the effect is context dependent for at least one input fall within the second category of "complex" regulatory functions, which are discussed below.

Figure 2A:
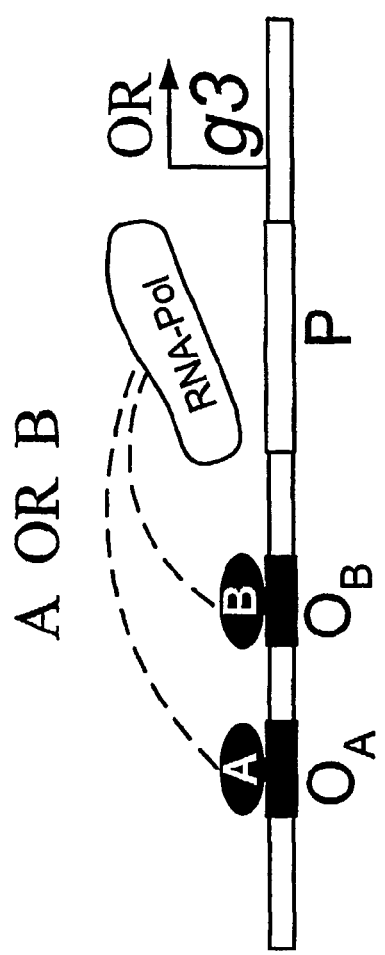
FIG. 2a is a schematic diagram showing the placement of two TF binding sites with respect to the promoter in a simple representation of an OR-gate.

Addressing first the simple regulatory functions, assume that TFs A and B each bind to a specific operator sequence in the vicinity of the promoter, as shown schematically in FIG. 2a. Further, assume that the TF concentrations $n_A$, $n_B$ are either very low, i.e. n≈0, or relatively high, e.g., n≈100-1000 molecules/cell, and that the gene expression level, P, in these states is also desired to be either very low, i.e., P≈0, or large, e.g., P≈0.5. Altogether, there are six "programmable" degrees of freedom: the binding thresholds $ñ_A$, $ñ_B$, the Boltzmann weight for promoter occupancy, $q_0$, and the mutual cooperativity factors between the TFs and the polymerase, i.e., $\omega_{AB}$, $\omega_{A0}$, and $\omega_{B0}$. (The index 0 is used for all quantities that refer to promotor/polymerase.) By malting different selections for these six variables, a number of gene regulatory logics can be implemented. In the corresponding equations, $q_A = n_A/ñ_A$, $q_B = n_B/ñ_B$, $q_{A'} = n_A/ñ_{A'}$, and $q_{B'} = n_B/ñ_{B'}$.

OR-gate: It is straightforward to realize the simple logical function A OR B, i.e., a high gene expression level when at least one of the "input signals" is present. For example, an OR-gate is useful for multi-purpose genes whose gene products are needed under different circumstances. It can be implemented by choosing strong binding sites for factors A and B (small ñ), indicated in FIG. 2a by the filled-in boxes under each of A and B, and placing them separately upstream of a weak promoter (small $q_0$), indicated by the open box. The dashed lines denote cooperative interaction. The column under node $g_3$ in the table of FIG. 1b lists the different possible conditions that can occur in the OR function.

FIG. 2b plots the fold-change or relative resulting expression level $P(n_A, n_B)$ (the change in promoter occupancy $P(n_A, n_B)$ relative to $P_{LOW}$, the lowest gene expression level over the entire range of $n_A$ and $n_B$. (Promoter occupancy is also known as RNAP binding probability.)) as a function of the TF concentrations for typical cellular TF concentrations in number of molecules per cell, determined according to:

$$Z_{OFF} = 1 + q_A + q_B + q_A q_B,$$

$$Z_{ON} = q_0(1 + \omega q_A + \omega q_B + 2\omega q_A q_B) \quad (9)$$

The corners of the plot represent the four different input states, i.e., (A, B)=(ON/OFF, ON/OFF). In this example, the parameters $ñ_A$, $ñ_B$=100, $q_0$=0.04, and $\omega$=20 were used. The ratio of the ON/OFF expression levels is, on average, about 9. For comparison, in the analysis of microarray mRNA expression data, fold changes in excess of two are usually considered significant, and typically range not much beyond twenty. The fold change obtained using the inventive method depends on the choice for $\omega$, the range over which the transcription factor concentrations are varied, and the promoter occupancy P desired in the ON-state. For the examples provided herein, $\omega$=20 and G must be greater than 0.4 in the ON-state. Qualitative results are insensitive to these choices, i.e., a significant fold-increase can always be obtained given $\omega$ in the reasonable range 10<$\omega$<100, and requires no fine-tuning of the parameters.

AND-gate: A AND B occurs only when both input signals are present. (See, e.g., Wade et al. (2001) for a well-studied naturally occurring example.) This function is particularly important for signal integration and can be achieved by choosing both TF binding sites to be relatively weak, then placing them upstream of a weak promoter, while allowing factors A and B to bind cooperatively by placing their sites adjacent to each other. Implementation of such an AND-gate is illustrated in FIG. 3a. In the figure, the open boxes corresponding to each of A, B and the promoter all indicate weak binding sites. The dashed lines indicate cooperative interaction. The column under node g2 in the table of FIG. 1b lists the different possible conditions that can occur in the AND function.

FIG. 3b provides the resulting expression level plot of relative RNAP binding probability dP for typical cellular TF concentrations ($\tilde{n}_A$, $\tilde{n}_B$=3500, $q_0$=0.027, $\omega$=20, which may be considered as the input-output characteristic of the system), represented by:

$$Z_{OFF}=1+q_A+q_B+\omega q_A q_B,$$

$$Z_{ON}=q_0(1+\omega q_A+q_B+2\omega^2 q_A q_B) \quad (10)$$

In this example, the average fold-increase between the OFF/ON-states is only about four-fold. This number would be greatly enhanced for synergistic factor-polymerase interaction. On the other hand, the non-synergistic factor-polymerase interaction is better suited for the OR-gate, since it can yield expression levels in the (A, B)=(ON, ON) state that are only slightly higher than in the states where only one factor is bound, similar to a digital OR-gate where these levels are equally high. In principle, it may be possible that the type of TF-polymerase interaction is also individually programmable through appropriate placement of the binding sites. However, the present model is preferably based only on very generic and biologically well-documented components and interactions. Note that the fold-increase of a gate can always be enhanced by introducing multiple binding sites for each TF to allow cooperative binding also among the same TF species, as in the well-studied example of the phage lambda lysis-lysogeny switch (Ptashne 1992).

NAND-gate—In the preceding two logic gate examples, regulatory regions are constructed so as to lead to the activation of gene expression in the presence of the TFs. Now consider the case where the gene is desired to be expressed in all states, unless both TFs are bound, i.e., $\overline{A \text{AND} B}$ (where the overline indicates "NOT"). It is well known in computer science that the NAND-gate is a universal gate from which, in principle, all logical functions can be constructed by cascading. In a biomolecular computer based on cis-regulatory gene control, this gate could be realized by placing the binding sites such that the TFs bind cooperatively with one another, but both bind competitively with polymerase. See FIG. 4a, where the hatched boxes corresponding to TFs A and B indicate moderate binding sites, while the promoter, indicated by a filled-in box is a strong binding site. The offset, overlapping boxes indicate mutual repression, and the dashed lines indicate cooperative interaction. The column under node $g_4$ in the table of FIG. 1b lists the different possible conditions that can occur in the NAND logic function. (A similar artificial realization of this regulatory function is presented by Dmitrova et al. (1998).)

Figures 4A, 4B:
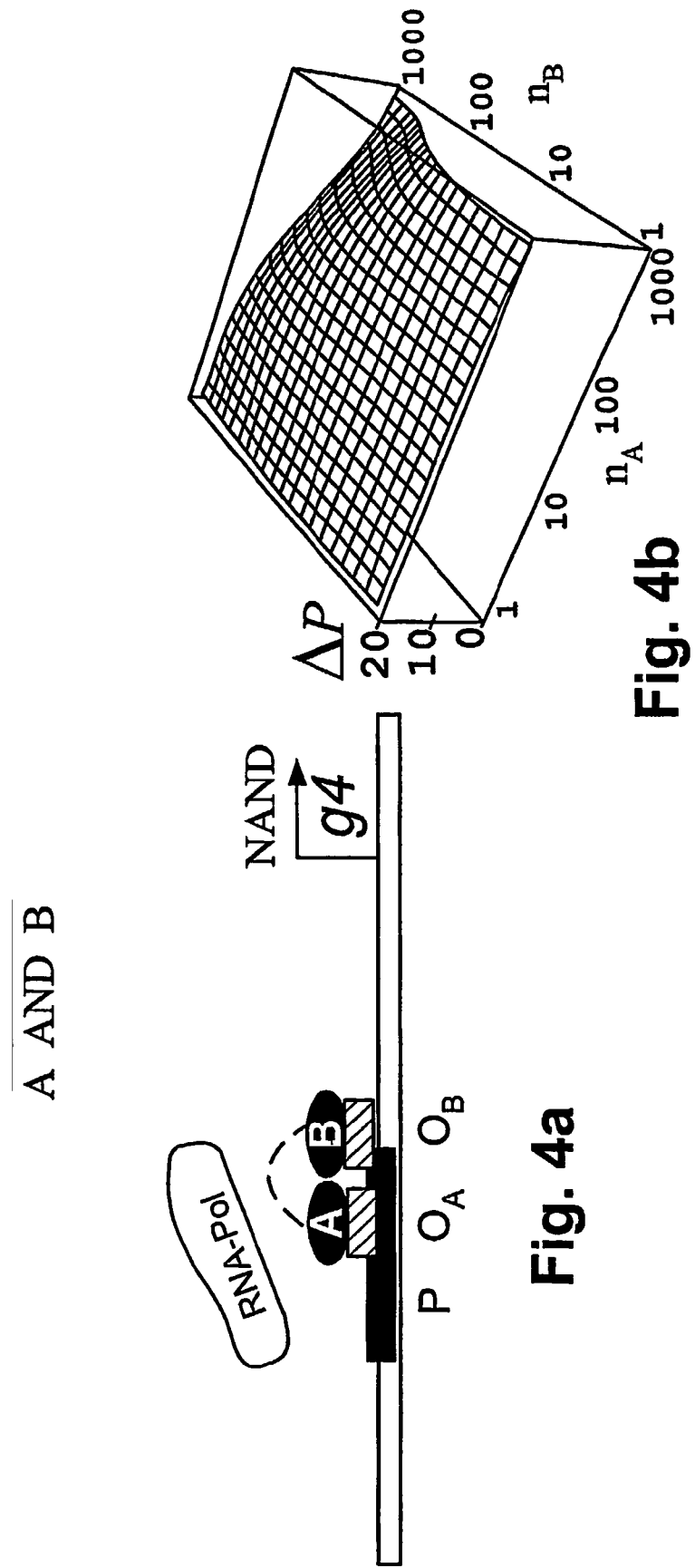

FIG. 4b shows the corresponding input-output characteristic (relative expression level), calculated according to:

$$Z_{OFF}=1+q_A+q_B+\omega q_A q_B,$$

$$Z_{ON}=q_0, \quad (11)$$

for a good set of binding thresholds: $\tilde{n}_A$, $\tilde{n}_B$=130, $q_0$=100, $\omega$=20. It can be seen that competitive binding with polymerase is quite effective as a repression mechanism, producing a 12-fold decrease in expression when both factors are present at a high level.

With two factors, there are four input states, (ON/OFF, ON/OFF), and in each of these states, low or high gene expression could be desired. Hence, there are $2^4$=16 different output patterns, each of which represents a two-factor logic. Exploiting symmetry and removing trivial gates that involve no or only one TF reduces this number to eight, three of which are discussed above. The five remaining logics are A∧$\overline{B}$, $\overline{A}$∧$\overline{B}$, A∨$\overline{B}$, A XOR B, and A EQ B. (The common shorthand notation ∧ is used for AND and ∨ for OR). The first three of the five can be implemented in exactly the same manner as the examples discussed above. The final two are complex regulatory functions where the qualitative effect of the inputs is context dependent. The XOR-gate allows expression if and only if one signal is present, and its inverse, the equivalence or EQ-gate, allows expression only when both inputs are low or both are high. Such logic gates cannot be represented by a schematic diagram as shown in FIG. 1a where there is only one operator site per TF.

XOR-gate: In one approach, for (A, B)=(OFF, OFF), the desired expression is low, such that a weak promoter is appropriate. When either A or B are present at a high level, strong expression is desired and, therefore, both binding sites should be strong and located such that they can recruit polymerase. This leaves no free parameter which could be selected such that expression is suppressed when (A, B)=(ON, ON).

Instead, there are multiple binding sites for the same factor within the same regulatory region, which is generally true for "complex" regulatory functions. In this case, the binding threshold can be set independently for each of these sites, since their sequences need not be the same. For example, there could be two sites that implement A∨B as in FIG. 2a and another pair of sites that shuts off gene expression when both factors are present, i.e., $\overline{A}$∧$\overline{B}$ as in FIG. 4a, which leads to the configuration shown in FIG. 5a. The column under node $g_5$ in the table of FIG. 1b lists the different possible conditions that can occur in the XOR function.

Figure 5B:
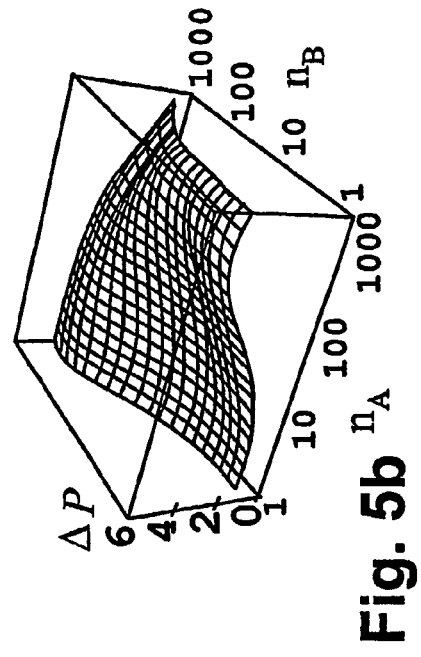

FIG. 5b illustrates the resulting relative promoter occupancy surface obtained from:

$$Z_{OFF}=(1+q_A+q_B+q_A q_B)\times(1+q_{A'}+q_{B'}+\omega q_{A'}q_{B'}),$$

$$Z_{ON}=q_0(1+\omega q_A+\omega q_B+2\omega q_A q_B) \quad (12)$$

which produces the saddle required for an XOR-gate. The parameters used in this plot were: $\tilde{n}_0$=6000, $\tilde{n}_A$, $\tilde{n}_B$=25, $\tilde{n}_{A'}$, $\tilde{n}_{B'}$=80.

Figure 5A:
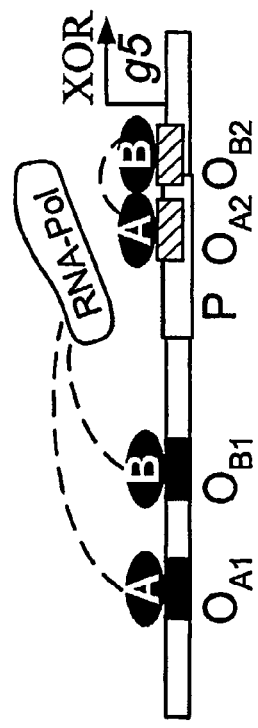
FIG. 5a is a schematic diagram showing the placement of two TF binding sites with respect to the promoter in a simple representation of an XOR-gate.
Figure 5D:
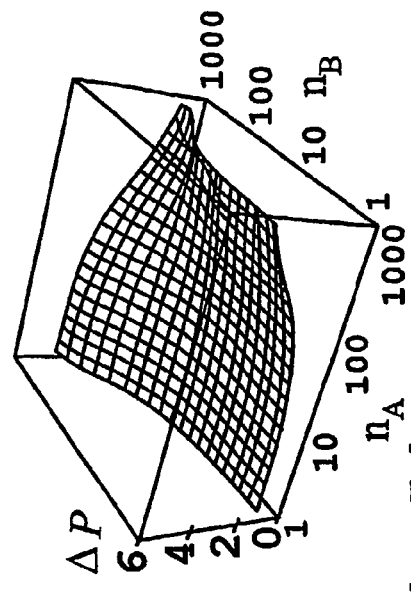
FIG. 5c is an alternative implementation of an XOR-gate using multiple promoters and FIG. 5d is the corresponding promoter occupancy plot.
Figure 5C:
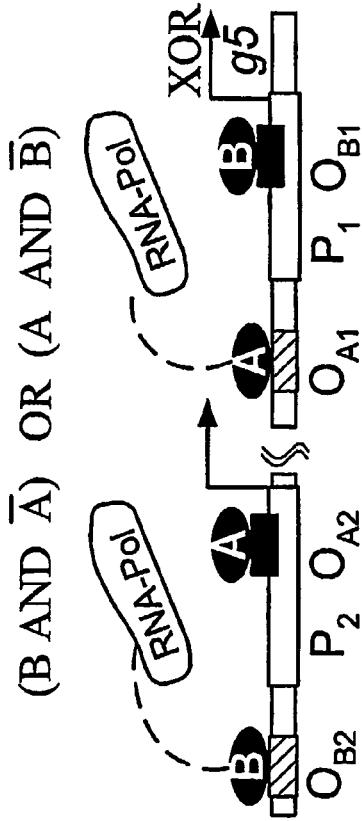

The arrangement shown in FIG. 5a is only one possible implementation of XOR. An alternative arrangement is illustrated in FIG. 5c, with its corresponding promoter occupancy results shown in FIG. 5d. In this case, a second promoter is introduced, making use of the fact that a gene can be transcribed from any one of a number of promoters (which are therefore connected by an OR-logic) and each promoter can have a separate regulatory region. (One well-studied example occurs in phage lambda where the λ-repressor gene is transcribed from two separate promoters, $P_{RE}$ for the establishment of lysogeny, and $P_{RM}$ for the maintenance (Ptashne 1992).]

Figure 6A:
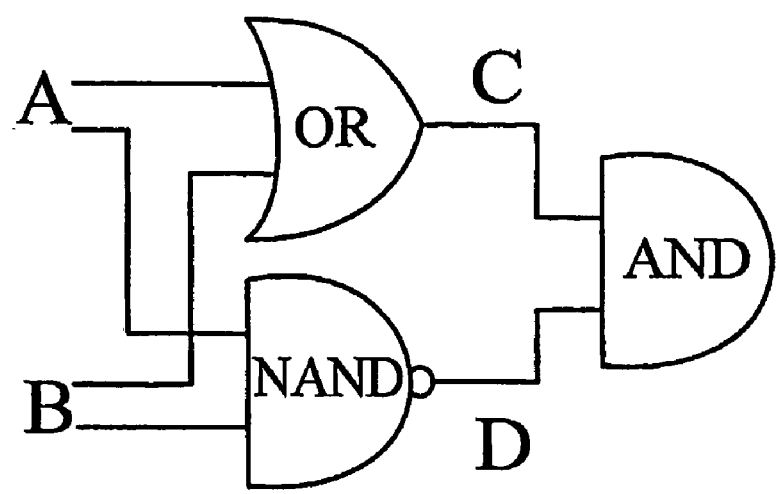
FIGS. 6a and b illustrate alternative implementations of an XOR-gate using (6a) a genetic network that cascades the simpler OR-, AND- and NAND-gates, and (6b) using a cofactor that simultaneously binds to factors A and B and covers their activating regions.

A digital electronic inspired solution would be to cascade several genes, each with a cis-regulatory logic of the simple type discussed above, i.e., the XOR-problem could be solved with the help of a small genetic network consisting of simple nodes. (This cascading strategy was recently used for the artificial design of regulatory functions through directed evolution (Guet et al. 2002).) For example, one could write A XOR B=(A ∨B) ∧$\overline{A}$ ∧$\overline{B}$ and introduce two new genes coding for transcription factors C and D that transmit the intermediate result from the OR- and the NAND-gate to the AND-gate, as illustrated in FIG. 6a. However, the empirical observation that natural cis-regulatory logics, at least in higher eukaryotes, are often much more complicated than the simple logics considered above (Arnone and Davidson 1997), suggests that cascading regulatory logics on a large scale may not be a favorable design. In fact, there are several plausible arguments against excessive cascading. First, the introduction of intermediate transcription factor genes is costly, since the total number of genes in an organism is limited. (For more complicated regulatory functions, a large number of intermediate genes would be required). Second, computation using intermediate gene products would be relatively slow, since the time lag between subsequent layers of computation due to transcription and translation is considerable. Finally, building complex logics by cascading multiple genes has the potential problem of synchronization, i.e., in order for the downstream genes to receive the correct inputs, the previous layer of genes must produce their outputs at more or less the same time.

Figure 6B:
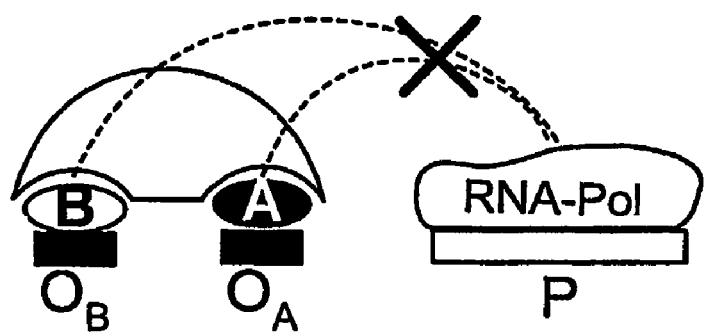

Other ways to produce an XOR-gate without the use of gene cascades involve allosteric transitions or specific cofactors. In general, these implementations reduce the potential for combinatorial control. One example, which makes use of a ubiquitous, i.e., unregulated, cofactor, is depicted in FIG. 6b. Here, the binding sites for factors A and B are closely spaced and can each activate gene expression, effectively realizing A OR B, but when both TFs are bound, a specific cofactor protein binds to them and covers their activating domains. Such cofactors are used for related purposes in nature (Alberts et al. 2002), however, extensive use of cofactors appears not to be a good general strategy. While this mechanism is more efficient in terms of resources and timing, it would require many very specific proteins and suffers from a reduced potential for combinatorial control. For example, if factors A and B implement the function A AND B for some other gene, the presence of the cofactor could interfere with the functioning of that gate.

Figure 7:
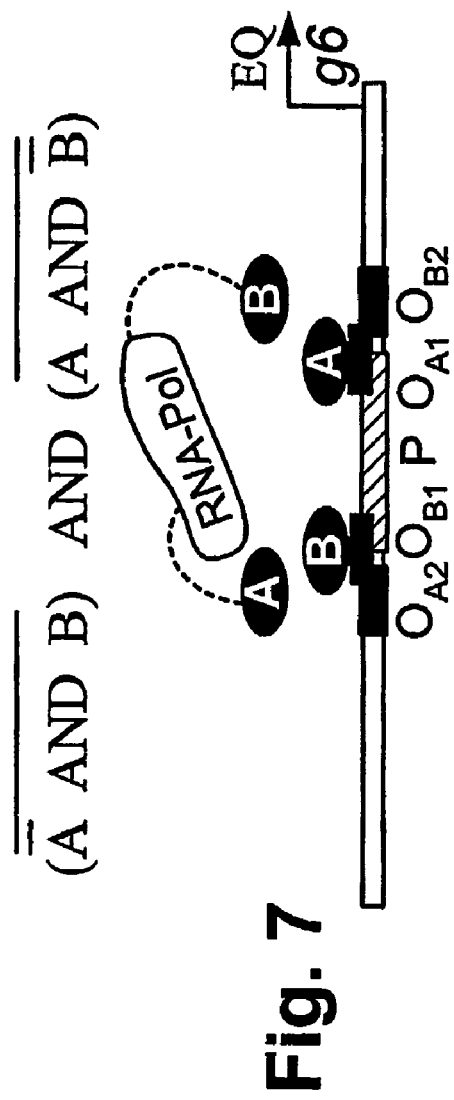
FIG. 7 is a simple representation of an EQ-gate illustrating the problem of promoter overcrowding.

EQ-gate: The EQ (equivalency)-gate illustrates a limitation of the present model which will be important for extensions to more complex, multi-factor logical functions. Consider the implementation of EQ-gate depicted in FIG. 7: a strong promoter is directly repressed by two flanking strong binding sites for A and B, whereas these binding sites themselves are repressed by flanking binding sites for the respective other TF. Effectively, this amounts to expressing EQ in the form $\overline{A}$ ∧$\overline{B}$ ∧$\overline{A}$ ∧$\overline{B}$. In principle, such an arrangement of binding sites would be able to produce the characteristic required for an EQ-gate, however, this implementation is based on a complicated arrangement of mutually overlapping sites crowded around the promoter, which raises doubts as to whether a functional gate could be realized in this manner in a cell, even disregarding the question of evolvability. Overcrowding is also illustrated in the response of gene $g_6$ indicated in FIG. 1b, where a strong promoter is required to turn the gene ON when neither of the TFs is activated, while repression is required under multiple conditions (i.e., when A is activated and B is not, and vice versa). It is difficult to implement both repressive conditions by the direct physical exclusion of RNAP as in FIG. 5a, given the small size of the promoter region.

Promoter overcrowding will prevent the design of more complex logical functions that require three or more repressor sites. One solution to this problem is a mechanism for long-distance repression which does not rely on direct competition between TFs and polymerase for DNA-binding in the promoter region. It is well-known that eukaryotes have evolved such mechanisms: For instance, protein complexes such as Tup1 in yeast, or *Groucho* in *Drosophila*, can be recruited by transcription factors bound distantly from the promoter to repress transcription (Courey and Jia 2001). These protein complexes have no DNA-binding domain themselves, but act as universal helping agents which can be recruited by many different TFs. The precise mechanism by which these protein complexes repress transcription is not well understood, but it appears to involve interference with the assembly of the transcription complex and chromatin remodeling agents.

Figure 8:
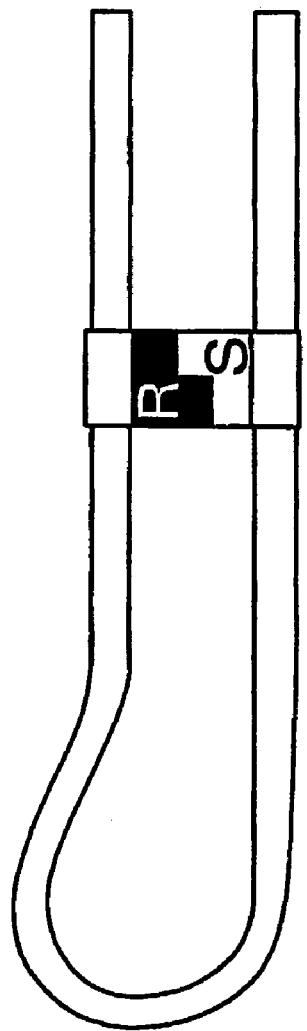
FIG. 8 is a schematic diagram illustrating distal regulation through DNA looping mediated by a heterodimer formed between two subunits R and S, each recognizing a distinct DNA binding site.

Another possible mechanism for long-distance repression would be through the use of a ubiquitous heterodimeric transcription factor (e.g., the L-arabinose operon of *E. coli* where AraC forms a homodimer (R. Schleif (2000).) Assume that it consists of two subunits, R and S, that each have a DNA-binding domain (with a different recognition sequence), and interact strongly through specific protein-protein contacts, as illustrated in FIG. 8. Further, assume that these subunits can bind cooperatively to nearby TFs in the same manner as for TF-TF interaction with a cooperativity factor of ω=20. The occupation of binding sequences for R in the regulatory region could then be controlled through TFs by cooperative or competitive binding. A binding sequence for subunit S would need to be in the vicinity of the promoter such that its occupation could interfere with polymerase binding. The subunit S would be recruited to its binding site through DNA-looping and protein-protein interaction with a bound subunit R. (Note that the protein-protein interaction between the two subunits of the heterodimer must be specific and different from the generic interaction between the TFs and polymerase. Otherwise, one of the subunits could mistakenly recruit polymerase instead of its partner. A cooperativity factor of ω=100 is used for this specific interaction (alternatively R and S could be tethered to each other). While existing implementations of this mechanism are not currently known, because the mechanism does not demand any novel components, it appears to be feasible to artificially engineer such a mechanism in bacteria.)

Figure 9B:
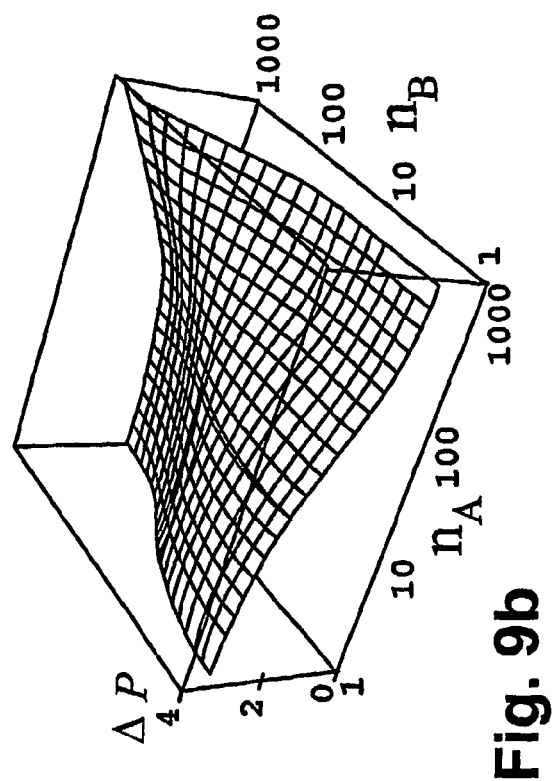
Figure 9A:
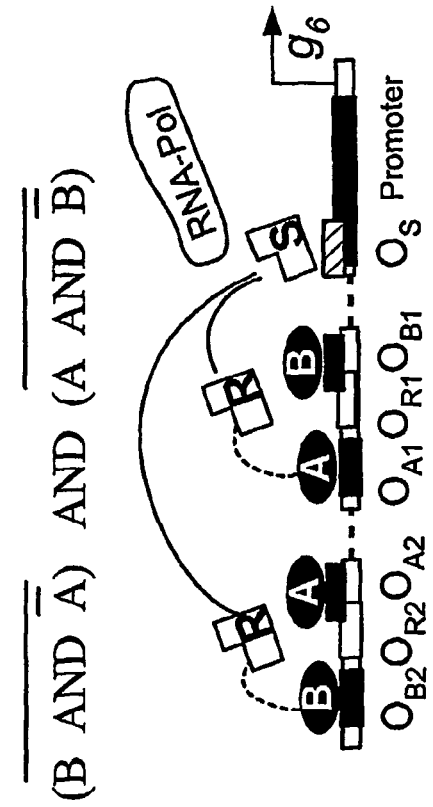
FIG. 9a is a schematic diagram showing the placement of two TF binding sites with respect to the promoter in a simple representation of an EQ-gate using DNA looping and repression.

Regardless of the precise mechanism, long-distance repression is a prerequisite for the design of more complex TF logics. An exemplary cis-regulatory implementation for the EQ-gate using the heterodimer-repression scheme is illustrated in FIG. 9a. When neither of the two repressor recruitment conditions $\overline{A}$ ∧B and A ∧$\overline{B}$ are satisfied, the polymerase transcribes from the strong promoter. The corresponding relative response characteristic $\Delta P(n_A, n_B)$ surface is shown in FIG. 9b as obtained from Equation (13) (a heterodimer repression scheme) using the following set of parameters: $\tilde{n}_0$=40, $\tilde{n}_R$, $\tilde{n}_{R'}$=20,000, $\tilde{n}_s$=30, $\tilde{n}_A$, $\tilde{n}_B$=100, $\tilde{n}_{A'}$, $\tilde{n}_{B'}$=1.

$$Z_{OFF} = (Q_R^- + Q_R^+)(Q_{R'}^- + Q_{R'}^+) + q_s[Q_R^- Q_{R'}^- + \omega_{RS}(Q_R^+ Q_{R'}^- + Q_R^+ Q_{R'}^-) + 2\omega_{RS} Q_R^+ Q_{R'}^+],$$

$$Z_{ON} = q_0(Q_R^- + Q_R^+)(Q_{R'}^- + Q_{R'}^+), \quad (13)$$

where $Q_R^- = (1+q_A)(1+q_B)$; $Q_R^+ = q_R(1+\omega q_A)$; $Q_{R'}^- = (1+q_B)(1+q_A)$; and $Q_{R'}^+ = q_{R'}(1+\omega q_B)$.

In Equation (13), $\omega_{RS}$ denotes the cooperativity between the two subunits of the heterodimer, which is assumed to be much larger than ω since it relies on specific protein-protein interactions. $q_S$, $q_R$, and $q_{R'}$ are the statistical weights for the occupation of the sites R, R' and S by the heterodimer. As with the weight $q_0$ for the occupation of the promoter, $q_S$, $q_R$, and $q_{R'}$, can be treated as programmable parameters since the heterodimer concentration is not a control variable.

Figure 9C:
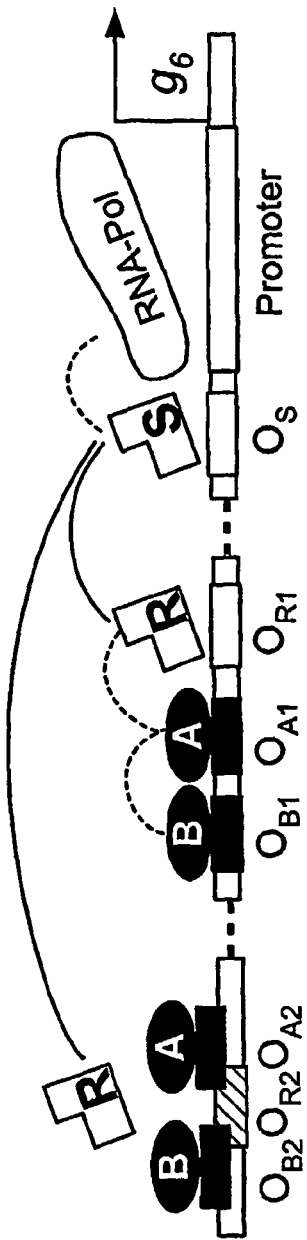
FIG. 9c is an alternative implementation of an EQ-gate using DNA looping similar to FIG. 9a and activation.

Alternatively, the EQ-gate can be implemented using a distal activation scheme as shown in FIG. 9c.

As long as the interaction between the TFs and RNAP is generic and glue-like, it is clear that one species of TF can be substituted for another by changing the TF-specific DNA binding sequences. More complex regulatory functions involving 3 or more inputs (TFs) can also be implemented using the described molecular apparatus by generalizing the construct of FIG. 9a or FIG. 9c.

Referring again to the realization of the EQ-gate using long-distance repression, it is apparent that the design depicted in FIG. 9a has a modular structure, with two repressive modules that suppress expression when certain conditions are met. (See Hartwell et al. (1999) for a general discussion of modular design in molecular biology.)

Figure 10A:
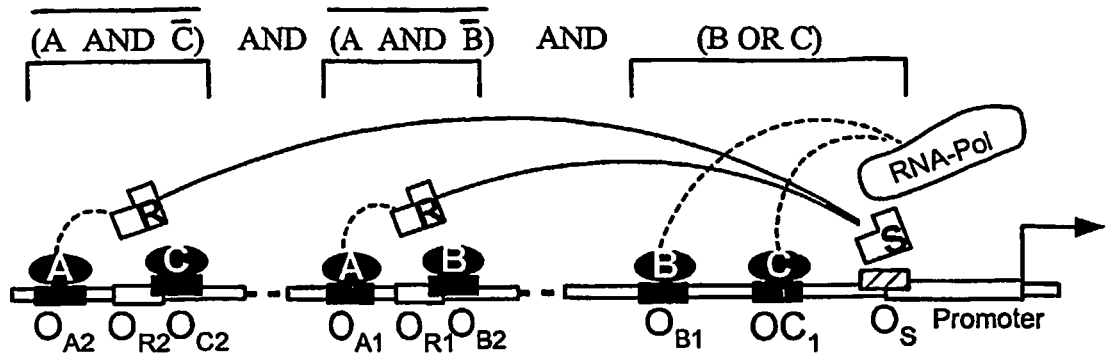
FIG. 10a is a schematic diagram of a construct of a regulatory function involving 3 controlling transcription factors with an activation module and two repression modules.

FIG. 10a illustrates the general architecture of the regulatory region one obtains using the distal repression mechanism. Gene expression occurs in this case if any one of the activation conditions is satisfied and none of the repression "clauses" is satisfied. The following approach can be taken: First, design an activating module, A, which assures that the expression level is high for at least all of the input states where it is desired to be high. Usually, one must activate expression for a larger set of states to facilitate the design of the activating module. Then, a number of (long-distance) repressive modules, $R_1$, $R_2$, . . . can be designed to specifically suppress expression in the input states that were unintentionally activated. Effectively, this amounts to writing an arbitrary logical function $F(X_1, X_2 \ldots X_M)$ of M input variables in the form $$F = \overline{R}_1 \wedge \ldots \wedge \overline{R}_{n-1} \wedge A \quad (14)$$

where $N \leq M$, and $A, R_1, R_2, \ldots$ are each logical functions of a subset of the variables $\{Xj\}$. Equation (14) simply expresses that the gene is transcribed whenever the activating module "fires" and none of the repressive modules fire, which resembles the conjunctive normal form (CNF) of Boolean algebra, $$F = C_1 \wedge C_2 \wedge \ldots \wedge C_N \quad (15)$$

where the clauses $C_i$ have the form $$C_n = (L_{n1} \vee L_{n2} \vee \ldots), \quad (16)$$

and each literal $L_{nj}$ can be any one of the variables $X_m$ or its complement $X_m^*$ (Whitesitt 1995). For any logical function F, one can systematically reduce the number of clauses and literals in Equation (15) with the Quine-McCluskey algorithm (or Karnaugh maps) (Unger 1997) to obtain the minimal CNF by applying distributivity and de Morgan's rule:

$$(\overline{B} \text{ OR } \overline{A}) \text{ AND } (\overline{C} \text{ OR } B) \text{ AND } (A \text{ OR } C), \quad (17)$$

where de Morgan's rule is $\overline{x_1 \text{AND} x_2} = \overline{x}_1 \text{ OR } \overline{x}_2$ for the Boolean variables $x_1$ and $x_2$. In fact, any logic function L of Boolean variables $x_1, x_2, \ldots x_N$ can be written in the CNF (J. E. Whitesitt, *Boolean Algebra and Its Applications* (Addison-Wesley, Reading Mass., 1961)), which generally consists of the logical AND of any number of "clauses" $C_1, C_2, \ldots$, i.e., $L = C_1 \text{ AND } C_2 \text{ AND } \ldots$, with each clause being the logical OR of $x_n$ or $\overline{x}_n$.

The function A can be identified as the clause in Equation (15) that contains the most literals, and the $R_n$ have the form $R_n = (L_{n1} \vee L_{n2} \vee \ldots)$. Then, function A would be implemented as a "row of activators" which are naturally connected by an OR-logic (one activator is sufficient for expression). More precisely, there could be one binding site for each factor that occurs in the clause A, where each site either cooperatively recruits or competitively binds a general activator, depending on whether the literal is positive or negative. The repressor modules $R_n$ naturally act by AND-logic, since transcription can only take place when none of them represses.

The inherent difficulty in this scheme is the design of the repressor modules, since the factors in the R-clauses are all connected by AND, i.e., they all need to cooperatively recruit or repel a general repressor, which quickly leads to a new overcrowding problem. However, the design of these modules could be greatly facilitated by again making use of heterodimers to obtain "action at a distance" through DNA-looping. Also, rather than trying to implement the minimal CNF, simple logical gates, which are straightforward to implement, could be used as the fundamental building blocks. This would require a different optimization scheme for the simplification of an arbitrary logical function, analogous to heuristic optimization schemes used for integrated circuit design.

Alternatively, one can generalize the distal activation scheme of FIG. 9c and arrive at the equivalent "disjunctive normal form" ("DNF"), $L = C'_1$, OR $C'_2$ OR . . . , with each clause C' being the logical AND of $x_n$ or $\overline{x}_n$. This form suggests a design using multiple promoters, similar to the example shown for the XOR-gate in FIG. 6a.

In the cis-regulatory implementation of logic functions, the input Boolean variables are the states of each species of TFs (e.g., whether a given TF species is phosphorylated). Implementation of all possible CNF requires both states of a TF to be DNA-binding, but each targeting a distinct DNA sequence. (Note that only the concentration of TFs in an activated state are considered. This feature is known to exist for a number of well-studied TFs such as CRP and AraC. (See, F. C. Neidhardt, Ed., *Escherichia coli* and *Salmonella: Cellular and Molecular Biology* (ASM Press, Washington D.C., 1996)). However, in many cases where the regulatory function is not overly complex, it is already sufficient if only one of the states of a TF is of the activated form.

The simple procedure described herein can be used for the cis-regulatory implementation of a wide range of logic functions: Reduce the desired logic function to the minimal CNF (or DNF), then implement one of the clauses as an activation clause and the remainder as repression clauses for CNF (or vice versa for DNF). Note that the CNF-like architecture requires a repression mechanism that dominates over activation, which can always be accomplished within the present method by adjusting the strengths of the binding sites as illustrated in the example of the EQ-gate of FIG. 9a. The DNF-like architecture based on long-distance activation is more natural whenever genes are repressed by default (e.g., through chromatin structure in eukaryotes). In addition, the two types of architecture can also be combined. Also note that the resulting architecture of the cis-regulatory region is naturally modular in the sense that the sub-sequence coding for a given clause can be moved to different positions in the regulatory region without affecting the regulatory function. This structure is reminiscent of the modular organization of cis-regulatory regions reported in a number of organisms. (E. H. Davidson, *Genomic Regulatory Systems* (Academic Press, San Diego Calif., 2001).).

It is well documented that different sets of regulatory proteins can work in combination to produce the same genetic responses, while the same set of regulatory proteins can be combined differently to produce different genetic responses, somewhat analogous to how different chemical elements can produce molecules of similar chemical properties (e.g., NaCl and KCl, while the same set of elements can make molecules of very different properties (e.g., graphite and diamond). The molecular components (TFs and RNAP) satisfying the two ingredients of regulated recruitment, i.e., continuously tuneable protein-DNA binding strengths and glue-like contact interaction between proteins, and further supplemented by distal activation and/or repression mechanisms, constitute a flexible toolkit, a kind of molecular Lego® set, which can be assembled in different combinations to perform a wide variety of complex logical computations.

While the present study was limited to the known mechanisms of transcription regulation in bacteria, qualitative aspects of the analysis may also be applicable to eukaryotic transcription which posses all of the key ingredients required for combinatorial control. For example, effective interaction can be obtained between two TFs by their competitive binding against a third protein or protein complex, e.g., nucleoid protein such as H-NS in bacteria or nucleosome complex in eukaryotes, referred to as the "collaborative competition" (K. J. Polach, J. Widom, *J. Mol. Biol.* 258, 800 (1996)). Also, distal activation and repression can be achieved in eukaryotes by the recruitment of various chromatin modification agents (K. Struhl, *Cell* 98, 1 (1999)).

At a qualitative level, the eukaryotic transcription machinery together with the regulated chromatin structure may present a better molecular platform to implement combinatorial signal integration, however, quantitative modeling and analysis of eukaryotic transcription is presently not as well developed. (See, A. Gilman, A. P. Arkin, *Annu. Rev Genonics Hum Genet.* 3, 341 (2002).)

The transcription apparatus appears to be a natural computing machine. The machine is effectively a general-purpose computer with a function that can be "programmed" at will through choices and placements of the protein-binding DNA sequences in the regulatory region. This can be contrasted with the alternative strategy of transcription control based on dedicated, complex (e.g., allosteric) molecular interactions. In the latter scheme, complexity of the system is derived from the complexity of proteins, while in the former, complexity is derived combinatorially from the composition of the regulatory sequences (the "software"), without the need for manipulating the proteins (the "hardware").

The inventive model assumes that all combination of inputs are physiologically relevant and actively selected, however, this in not always going to be the case. A typical "logic table" for a multiply-regulated gene might have many "don't care" conditions (which makes the design of cis-regulatory control even easier.) On the other hand, the experimentally determined response characteristics might contain some unexpected bumps and dips which would suggest the existence of previously unidentified physiological demand on the gene.

The inventive model disclosed herein, with its tunable strength of the binding sequences and selective TF-TF interaction, can be used as a starting point for analysis of gene expression data generated by the DNA microarray technology. In these problems, one typically has some idea of the activity of the input TFs (through the mRNA expression levels of the corresponding genes) and also the activity of the regulated gene for a number of different physiological conditions. The inventive model can then be used to find the parameters $n_i$ and $w_{ij}$ that are consistent with the data. This approach can be viewed as a nonlinear generalization of the method used by Reinitz and collaborators to find parameters of their genetic network based on gene expression data. The inventive method relies on (i) the identification of the TF-binding motifs in the regulatory region of each studied gene, and (ii) the assumption of a simple form of protein-protein interaction. The numerous ongoing bioinformatics as well as experimental studies (e.g., with the use of dsDNA arrays) to identify binding sequence motif will provide abundant information on binding sequences in the near future. While the lack of detailed information on protein interaction in general may present an obstacle, the insensitivity of the inventive model to the details of protein interaction suggest that it can nevertheless be used to capture the essential behavior of different regulatory functions.

The precise molecular interactions that lead to the complex transcription control observed e.g. by Yuh et al. (2001) are not understood in detail. However, one can expect a complex underlying network of interactions between DNA-bound proteins similar to, but more complicated than, the example shown in FIG. 10. Within the inventive model, the notion of a "molecular network" can in fact be made more explicit: When written in the general Ising model form as in Equation (8), the inventive model is essentially equivalent to the "Boltzmann machine" model of neural networks (Hertz et al. 1991), since the interactions in the model are based on equilibrium statistical mechanics. In this sense, a single node of a gene regulatory network is already a network in itself.

Figure 10B:
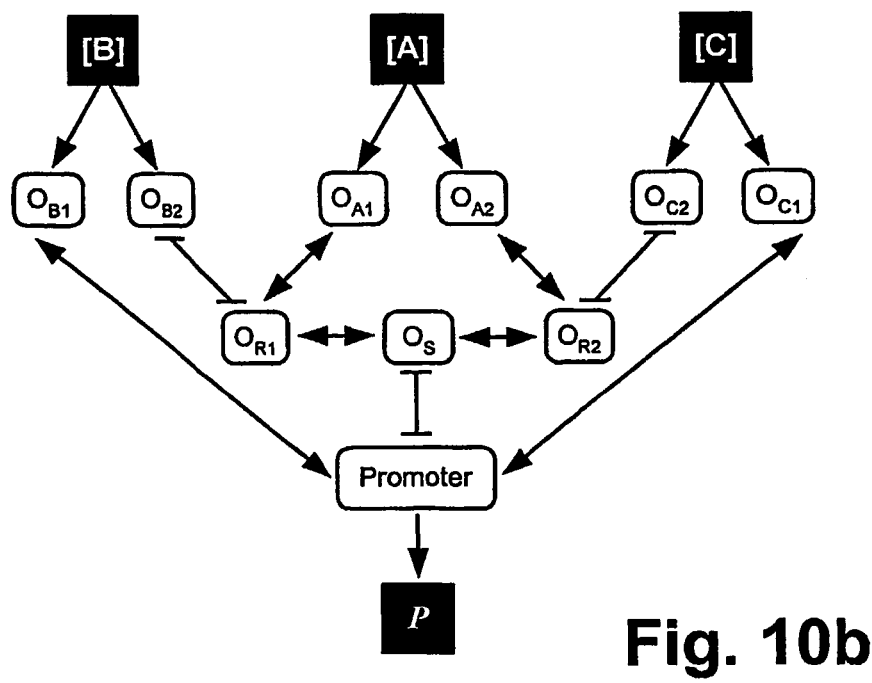
FIG. 10b is a schematic diagram showing the construct of FIG. 10a mapped to a Boltzmann machine.

Analogy to the neural network model can help illustrate certain features of the inventive model. The occupancy of a binding site corresponds to the state of a neuron (firing or not) and the binding strength of a site becomes the "firing threshold". Molecular interactions between the proteins play the role of "synapses" which transduce signals between the neurons. This artificial "neural network" is distinguished by two unique features: synaptic connections are symmetric (since molecular interactions are symmetric), and each input can project to multiple neurons, allowing for "hidden units" in the network. In the present model, these hidden units correspond to the greater number of binding sites than the number of involved TFs, thus allowing for the implementation of "complex" regulatory functions to perform computations such as XOR (Hertz et al. 1991; Minsky and Papert 1969). This is illustrated in FIG. 10b, where the site R1, R2 and S correspond to hidden units.

In terms of the neural network language, designing a regulatory function means "training" the net to produce certain responses in the output unit (the promoter) given different patterns of input signals (the TF concentrations). This theoretical framework allows the incorporation of many useful results obtained in the study of neural nets. In particular, it can be used to explore quantitatively the issue of cross-talk which will be important for a large network controlled by the same set of TFs.

According to the inventive model, a wide class of different regulatory functions can be readily implemented by selecting and juxtaposing binding sequences in the cis-regulatory region of genes. This leads to the possibility of artificial implementation of complex logic finctions via de novo synthesis of gene regulatory regions (Elowitz and Leibler 2000; Gardner et al. 2000; Guet et al. 2002). Furthermore, protein components could be artificially designed to satisfy the assumptions of inventive model. For example, to obtain promiscuous interaction between many TFs, one could design them by fusing the same cooperative binding domains (taken from a well-characterized TF, e.g., the lambda-repressor) to the different DNA-binding domains taken from different TFs. Given the protein components, the strengths and placement of the binding sites required to accomplish a given logic function can be determined in silico. Such a construct can then be put on a plasmid, and the regulatory function can be fine-tuned via "directed evolution". Finally, such logic "devices" can be interconnected (Guet et al. 2002) in a combinatorial way to implement artificial genetic networks. The advantage of the present approach is that with complex signal integration at each node, the number of gene cascades needed to carry out a desired function can be minimized. For example, digital counters can be constructed much more efficiently by combining the XOR and AND functions, and feeding their output to each other, than by using only inverters.

From an evolutionary perspective, the above-described results suggest that promiscuous protein-protein interactions paired with specific DNA-protein interaction may be the underlying general and flexible mechanism for transcription control, while specific protein-protein interactions may have evolved for fine tuning whenever there is less of a demand on combinatorial control. Presumably, different implementations of a given regulatory logic will differ in the degree of evolvability. Accordingly, some implementations will be able to adapt more easily (through simple evolutionary processes such as point-mutations, insertions, deletions, recombination, etc.) to a change in the selective pressure which, for example, could suddenly favor a different regulatory logic than the one presently realized. Hence, in an attempt to understand the benefits of one design for gene regulation over another, the issue of evolvability can play an important role.

Different designs could reflect different evolutionary history, i.e., different time dependences of the functional demand. As an example, the implementation of XOR in FIG. 5a could have evolved from an ancestral OR function, with the repressive NAND module added on subsequently when additional selection arose. A very different evolution trajectory would be required to produce the alternative implementation of XOR function depicted in FIG. 6(a).

The method of characterizing a transcription regulation system quantitatively includes the step of obtaining the response characteristics. If those characteristics permit a reduced binary description, a representation of the regulatory function is found in terms of binary logic. To obtain the response characteristics experimentally, the concentration of all of the relevant TFs must be controlled, and the transcription level measured for each of the combination of TF concentrations, irrespective of the functional demand.

The inventive model assumes completely promiscuous protein-protein interactions and treats only the protein-DNA interactions as specific. The operator and promoter sequences in the genomic DNA are then the only "programmable" objects in the model: their sequence determines the protein-DNA binding affinity, whereas their placement determines the interaction among the bound proteins. These programmable variables, the binding sequences and their placement, can be chosen at will for the design of an artificial cis-regulatory logic. (For natural gene regulation this choice is made by evolution, in a dynamic process involving mutation, recombination, and selection.)

The inventive model provides the ability to "program" genetic response at will by constructing designer regulatory sequences (of the order of several hundred bases for bacteria and several thousand bases for eukaryotes), which offers a number of potentially lucrative bioengineering and biomedical applications. By inserting a designed regulatory region controlling a reporter gene (e.g., the green fluorescence protein or GFP) into a population of bacteria equipped with a number of special chemical detectors, one can program these bacteria to look for and report unique patterns of detected traits that correspond to specific chemical pollutants or biological warfare agents in the environment. It is well known that feature discrimination schemes based on multiple rather than single trait can drastically improve the accuracy of discrimination. Also, the combinatorial power of signal integration allows the same bacteria be programmed to report on different patterns of detected traits, making them a multi-purpose warning system.

These approaches can also be applied to molecular medicine: A major challenge in modern medicine is the accurate delivery and controlled release of drugs (or genes in the case of gene therapy) to the intended target in order to minimize "collateral damage". This is a difficult task because the current strategies primarily focus on a single feature of the target, e.g., cells with a particular type of receptors, cells that grow abnormally fast, etc. With programmable genetic elements, it will be possible to monitor a multiple set of features and integrate the detected information for much more accurate target recognition, analogous to what "smart bombs" have done in modern warfare. For example, one can program the regulatory sequences to turn on a reporter gene only if the pattern of regulatory protein activities in a cell matches with one of those unique to tumor cells. (Large collections of such patterns are available publicly from DNA micro-array studies.) The reporter gene can then serve as the indicator of tumor cells and guide external treatment such as radiation or surgery. Alternatively, one can replace the reporter gene by a killer gene, e.g., p53, to trigger programmed cell-death once a tumor-specific pattern is detected. The "targeted delivery" problem associated with gene therapy can be largely circumvented using the "smart" regulatory system: The therapeutic gene can be delivered indiscriminately to all cell types since the programmed regulatory sequence will limit activation to those that have entered the targeted cells; all others would be inactive and naturally disappear by attrition over time. If one can further incorporate such programmed therapeutic genes together with special purpose detectors into a cell, then one can in principle turn these special cells into "miniature medical stations" to monitor vital signs and provide treatment or warning when problems are detected, e.g., turn on an insulin gene when extraordinary level of glucose level is detected in the blood.

Other embodiments and modifications of the present invention will occur readily to those of ordinary skill in the art in view of these teachings. Therefore, this invention is to be limited only by the following claims which include all such other embodiments and modifications when viewed in conjunction with the above specification and accompanying drawings.

REFERENCES

Incorporated Herein by Reference

1. Alberts, B., A. Johnson, J. Lewis, M. Raff, K. Roberts, and P. Walter. 2002, *Molecular Biology of the Cell* (Garland Publishing, Inc.), 4th edition.
2. Arnone, M. I., and E. H. Davidson. 1997, *Development* 124, pp. 1851-1864.
3. Courey, A. J., and S. T. Jia. 2001, *Genes Dev.* 15, pp. 2786-2796.
4. Davidson, E. H., J. P. Rast, P. Oliveri, A. Ransick, C. Calestani, C. H. Yuh, T. Minokawa, G. Amore, V. Hinman, C. Arenas-Mena, O. Otim, C. T. Brown, et al., 2002, *Science* 295, pp. 1669-1678.
5. Davidson, E. H., *Genoinic Regulatory Systems*, 2001, Academic Press, San Diego Calif.
6. Dmitrova, M., G. Younes-Cauet, P. Oertel-Buchheit, D. Porte, M. Schnarr, and M. Granger-Schnarr. 1998, *Mol. Gen. Genet.* 257, pp. 205-212.
7. Elowitz, M. B., and S. Leibler. 2000, *Nature* 403, pp. 335-338.
8. Frankel, A. D., and P. S. Kim. 1991, *Cell* 65, pp. 717-719.
9. Gardner, T. S., C. R. Cantor, and J. J. Collins. 2000, *Nature* 403, pp. 339-342.
10. Gerland, U., J. D. Moroz, and T. Hwa. 2002, *Proc. Nat. Acad. Sci. U.S.A.*

11. Gilman, A., Arkin, A. P., 2002, *Annu Rev Genomics Hum Genet.* 3, 341.
12. Guet, C. C., M. B. Elowitz, W. Hsing, and S. Leibler. 2002, *Science* 296, pp. 1466-1470.
13. Hartwell, L. H., J. J. Hopfield, S. Leibler, and A. W. Murray. 1999, *Nature* 402, pp. C47-C52.
14. Hertz, J., A. Krogh, and R. Palmer, 1991, *Introduction to the Theory of Neural Computation* (Addison-Wesley, USA).
15. von Hippel, P. H., and O. G. Berg. 1986, Proc. Natl. Acad. Sci. U.S.A. 83, pp. 1608-1612.
16. Ideker, T., V. Thorsson, J. A. Ranish, R. Christmas, J. Buhler, J. K. Eng, R. Bumgarner, D. R. Goodlett, R. Aebersold, and L. Hood. 2001, *Science* 292, pp. 929-934.
17. Joung, J. K., D. M. Koepp, and A. Hochschild. 1994, Science 265, pp. 1863-1866.
18. Kalir, S., J. McClure, K. Pabbaraju, C. Southward, M. Ronen, S. Leibler, M. G. Surette, and U. Alon. 2001, *Science* 292, pp. 2080-2083.
19. Kauffman, S. A., *The Origins of Order: Self-Organization and Selection in Evolution,* 1993, Oxford University Press.
20. Li, R., H. Pei, and D. K. Watson. 2000, *Oncogene* 19, pp. 6514-6523.
21. McClure, W. R. 1980, *Proc. Natl. Acad. Sci. U.S.A.* 77, pp. 5634-5638.
22. Minsky, M. L., and S. A. Papert. 1969, *Perceptrons* (MIT Press, Cambridge, USA).
23. Misteli, T., 2001, *Science* 291, pp. 843-847.
24. Neidhardt, F. C., Ed., *Escherichia coli and Salmonella: Cellular and Molecular Biology,* 1996, ASM Press, Washington D.C.
25. K. J. Polach, J. Widom, 1996, *J. Mol. Biol.* 258, 800
26. Ptashne, M. 1992, *A genetic switch: phage lambda and higher organisms* (Blackwell Scientific, Cambridge, Mass.).
27. Ptashne, M., and A. Gann. 1997, *Nature* 386, pp. 569-577.
28. Ptashne, M., and A. Gann. 1998, *Curr. Biol.* 8, pp. R812-R822.
29. Ptashne, M., and A. Gann. 2002, *Genes and signals* (Cold Spring Harbor Laboratory Press, Cold Spring Harbor, N.Y.).
30. Reinitz, J., Kosman, D., Vanario-Alonso, C. E., and Sharp, D. H., 1998, *Dev. Genet.* (Amsterdam) 23, pp. 11-27.
31. Ren, B., F. Robert, J. J. Wyrick, O. Aparicio, E. G. Jennings, I. Simon, J. Zeitlinger, J. Schreiber, N. Hannett, E. Kanin, T. L. Volkert, C. J. Wilson, et al. 2000, *Science* 290, pp. 2306-+.
32. Shea, M. A., and G. K. Ackers. 1985, *J. Mol. Biol.* 181, pp. 211-230.
33. Stormo, G. D., and D. S. Fields. 1998, *Trends Biochem. Sci.* 23, pp. 109-113.
34. Struhl, K., 1999, *Cell* 98, 1
35. Unger, H. 1997, *The Essence of Logic Circuits* (IEEE Press).
36. Wade, J. T., T. A. Belyaeva, E. I. Hyde, and S. J. W. Busby. 2001, *Embo J.* 20, pp. 7160-7167.
37. Whitesitt, J. 1995, *Boolean Algebra and Its Applications* (Dover Publications).
38. Wolberger, C. 1999, *Ann. Rev. Biophys. Biomol. Struct.* 28, pp. 29-56.
39. Wolf, D. M., and F. H. Eeckman. 1998, *J. Theor. Biol.* 195, pp. 167-186.
40. Yuh, C. H., H. Bolouri, and E. H. Davidson. 2001, *Development* 128, pp. 617-629.

What is claimed is:

1. A method for combinatorially controlling the transcription of a target gene in a cell for producing a programmed response in the cell, the method comprising:

identifying a plurality of logic functions, wherein each logic function combines two or more different inputs to generate an output comprising a unique gene expression in the cell;

implementing at least one selected logic function that produces a desired genetic response when a combination of specified conditions are present, wherein the two or more different inputs comprise two or more regulatory proteins and the at least one selected logic function is implemented by producing interactions between the two or more regulatory proteins and interactive binding of the two or more regulatory proteins at DNA binding sites of the target gene to control a probability of promoter occupancy, wherein the target gene comprises one or more cis-regulatory regions having individual DNA binding sites, and wherein each DNA binding site has a binding strength and a binding location which are adjustable by varying composition of the one or more cis-regulatory regions to select one of a cooperative binding and competitive binding of the two or more regulatory proteins at the binding sites and one of a cooperative binding and competitive binding between the two or more regulatory proteins and polymerase;

wherein the interactions comprise contact interactions and long-distance interactions that avoid interference between the DNA binding sites;

wherein the desired genetic response in the cell comprises reporting or treatment of a disease or condition in which the two or more regulatory proteins are expressed; wherein each step of the method is executed on a transcription apparatus which corresponds to a computing machine;

wherein the probability of promoter occupancy is determined according to the relationship $P_{po}=Z_{ON}/(Z_{ON}+Z_{OFF})$, where $Z_{ON}$ and $Z_{OFF}$ are the total statistical weight of all states in which the promoter is occupied and unoccupied, respectively;

wherein when the selected logic function is AND, $Z_{ON}=q_o(1+\omega q_A+q_B+2\omega^2 q_A q_B)$ and $Z_{OFF}=1+q_A+q_B+\omega q_A q_B$;

wherein when the selected logic function is OR, $Z_{ON}=q_o(1+\omega q_A+\omega q_B+2\omega q_A q_B)$ and $Z_{OFF}=1+q_A+q_B+q_A q_B$;

wherein when the selected logic function is XOR, $Z_{ON}=q_o(1+\omega q_A+\omega q_B+2\omega q_A q_B)$ and $Z_{OFF}=(1+q_A+q_B+q_A q_B)\times(1+q_A+q_B+\omega q_A q_B)$; and wherein when the selected logic function is NAND, $Z_{ON}=q_o$ and $Z_{OFF}=1+q_A+q_B+\omega q_A q_B$;

where $q_o$ is the Boltzmann weight for promoter occupancy, $q_A$ and $q_B$ are ratios of the regulatory protein concentrations to the binding thresholds for input A and input B, respectively, and w is the mutual cooperativity factor.

2. The method of claim 1, wherein the one or more cis-regulatory regions are modular.

3. The method of claim 1, wherein at least some of the interactions among the regulatory proteins comprise non-specific protein-protein interactions controlled by selecting the binding locations.

4. The method of claim 1, wherein at least some of the interactions among the regulatory proteins comprise specific protein-protein interactions.

5. The method of claim 1, wherein at least some of the interactions among the regulatory proteins comprise protein-protein interactions mediated by collaborative competition between the regulatory proteins and a glue-like DNA-bound protein or protein complex.

6. The method of claim 1, wherein the interactive binding comprises tunable-specific protein-DNA interactions which are tunable by selecting the binding strengths.

7. The method of claim 1, wherein the one or more cis-regulatory regions include long distance repression and activation schemes.

8. The method of claim 1, wherein the step of implementing the at least one logic function further comprises:
    reducing the at least one logic function to a minimal conjunctive normal form; and
    implementing a first clause as an activation clause and all remaining clauses as repression clauses;
    wherein the relative binding strength is selected so that repression dominates activation.

9. The method of claim 1, wherein the step of implementing the at least one logic function further comprises:
    reducing the at least one logic function to a minimal disjunctive normal form; and
    implementing a first clause as a repression clause and all remaining clauses as activation clauses.

10. The method of claim 1, wherein the disease or condition is cancer and the desired genetic response is activation of a reporter gene.

11. The method of claim 1, wherein the disease or condition is cancer and the desired genetic response is activation of a killer gene.

12. The method of claim 1, wherein the disease or condition is exposure to an external chemical or biological agent and the desired genetic response is activation of a reporter gene.

13. The method of claim 1, wherein desired genetic response is activation of a drug receptor of a drug for treatment of the disease or condition.

14. A method for combinatorial transcription control for controlling gene expression in a cell for producing a programmed response in the cell, the method comprising:
    identifying a plurality of logic functions, each logic function having two or more different inputs and an output comprising a unique and artificial genetic response;
    selecting at least one logic function that produces a desired genetic response; and
    implementing the at least one logic function by producing interactions among different inputs comprising two or more transcription factors and controlling interactive binding of the two or more transcription factors at corresponding binding sites of one or more target genes, wherein the target genes each comprise one or more cis-regulatory regions having individual DNA binding sites, and wherein each binding site has a binding strength and a binding location which are adjustable by varying composition of the one or more cis-regulatory regions to select one of a cooperative interaction and competitive interaction between the two or more transcription factors and to select cooperative or competitive binding of between the two or more transcription factors and polymerase, all to control a probability of promoter occupancy;
    generating the desired genetic response in the cell as the output, wherein the desired genetic response in the cell comprises reporting or treatment of a disease or condition in which the two or more transcription factors are expressed; wherein each step of the method is executed on a transcription apparatus which corresponds to a computing machine;
    wherein the probability of promoter occupancy is determined according to the relationship $P_{po} = Z_{ON}/(Z_{ON} + Z_{OFF})$, where $Z_{ON}$ and $Z_{OFF}$ are the total statistical weight of all states in which the promoter is occupied and unoccupied, respectively;
    wherein when the selected logic function is AND, $Z_{ON} = q_o (1 + \omega q_A + q_B + 2\omega^2 q_A q_B)$ and $Z_{OFF} = 1 + q_A + q_B + \omega q_A q_B$;
    wherein when the selected logic function is OR, $Z_{ON} = q_o (1 + \omega q_A + \omega q_B + 2\omega q_A q_B)$ and $Z_{OFF} = 1 + q_A + q_B + q_A q_B$;
    wherein when the selected logic function is XOR, $Z_{ON} = q_o (1 + \omega q_A + \omega q_B + 2\omega q_A q_B)$ and $Z_{OFF} = (1 + q_A + q_B + q_A q_B) \times (1 + q_A + q_B + \omega q_A q_B)$; and
    wherein when the selected logic function is NAND, $Z_{ON} = q_o$ and $Z_{OFF} = 1 + q_A + q_B + \omega q_A q_B$;
    where $q_o$ is the Boltzmann weight for promoter occupancy, $q_A$ and $q_B$ are ratios of the regulatory protein concentrations to the binding thresholds for input A and input B, respectively, and w is the mutual cooperativity factor.

15. The method of claim 14, wherein the one or more cis-regulatory regions are modular.

16. The method of claim 14, wherein at least some of the interactions among the transcription factors comprise non-specific protein-protein interactions controlled by selecting the binding locations.

17. The method of claim 14, wherein at least some of the interactions among the transcription factors comprise specific protein-protein interactions.

18. The method of claim 14, wherein at least some of the interactions among the transcription factors comprise protein-protein interactions mediated by collaborative competition between the transcription factors and a glue-like DNA-bound protein or protein complex.

19. The method of claim 14, wherein the interactive binding comprises tunable-specific protein-DNA interactions which are tunable by selecting the binding strengths.

20. The method of claim 14, wherein the cis-regulatory region includes long distance repression and activation schemes that avoid interference between the DNA binding sites.

21. The method of claim 14, further comprising, after the step of identifying the at least one logic function:
    reducing the at least one logic function to a minimal conjunctive normal form; and
    implementing a first clause as an activation clause and all remaining clauses as repression clauses;
    wherein the binding strength is selected so that repression dominates activation.

22. The method of claim 14, further comprising, after the step of identifying the at least one logic function:
    reducing the at least one logic function to a minimal disjunctive normal form; and
    implementing a first clause as a repression clause and all remaining clauses as activation clauses.

23. The method of claim 14, wherein the disease or condition is cancer and the desired genetic response is activation of a reporter gene.

24. The method of claim 14, wherein the disease or condition is cancer and the desired genetic response is activation of a killer gene.

25. The method of claim 14, wherein the disease or condition is exposure to an external chemical or biological agent and the desired genetic response is activation of a reporter gene.

26. The method of claim 14, wherein desired genetic response is activation of a drug receptor of a drug for treatment of the disease or condition.

27. A method of combinatorially controlling gene expression in a cell by encoding control functions in regulatory DNA sequences for producing a programmed response in the cell, the method comprising:

selecting a relative binding strength and a relative binding position of individual DNA binding sites within a cis-regulatory region of one or more regulatory DNA sequences to exert combinatorial control of gene expression to operate as at least one logic function selected from a plurality of different logic functions for combining two or more inputs, each input comprising a different regulatory protein, to generate an output comprising a programmed gene expression upon DNA binding of two or more different regulatory proteins as determined by the selected relative binding strength and relative binding position of the DNA binding sites to control probability of promoter occupancy, wherein each different logic function produces a different programmed gene expression in the cell; and wherein the programmed gene expression in the cell comprises reporting or treatment of a disease or condition in which the two or more different regulatory proteins are expressed.

28. The method of claim 27, wherein the control functions are modular.

29. The method of claim 27, wherein the relative binding strengths and relative binding sites within the cis-regulatory region are selected to produce tunable specific DNA-protein interactions and non-specific, glue-like protein-protein interactions.

30. The method of claim 29, further comprising selecting the relative binding strengths and relative binding sites to permit distal activation and repression.

31. The method of claim 27, wherein the disease or condition is cancer and the desired genetic response is activation of a reporter gene.

32. The method of claim 27, wherein the disease or condition is cancer and the desired genetic response is activation of a killer gene.

33. The method of claim 27, wherein the disease or condition is exposures to an external chemical or biological agent and the desired genetic response is activation of a reporter gene.

34. The method of claim 27, wherein desired genetic responses is activation of a drug receptor of a drug for treatment of the disease or condition.

35. A method for combinatorial control of gene expression to produce a programmed genetic response in a cell, the method comprising:

producing a plurality of different glue-like contact interactions between two or more transcription factors at DNA binding sites of genes for selectively activating or repressing expression in a target gene under specified conditions that comprise to inputs into one or more logic functions, wherein the one or more logic functions are selected according to a relationship between the two or more transcription factors and a disease or condition, wherein each DNA binding site has a protein-DNA binding affinity and a binding location that are variable by varying a cis-regulatory sequence at the DNA binding site to select a predetermined combination of degrees of freedom selected from the group consisting of DNA binding thresholds for each transcription factor, Boltzmann weight for promoter occupancy, and mutual cooperativity factors between the transcription factors and RNA polymerase, wherein the predetermined combination of degrees of freedom controls a probability of promoter occupancy to produce a desired genetic response in the cell; and wherein the desired genetic response in the cell comprises reporting or treatment of the disease or condition in which the two or more transcription factors are expressed; wherein each step of the method is executed on a transcription apparatus which corresponds to a computing machine;

wherein the probability of promoter occupancy is determined according to the relationship $P_{po}=Z_{ON}/(Z_{ON}+Z_{OFF})$, where $Z_{ON}$ and $Z_{OFF}$ are the total statistical weight of all states in which the promoter is occupied and unoccupied, respectively;

wherein when the selected logic function is AND, $Z_{ON}=q_o(1+\omega q_A+q_B+2\omega^2 q_A q_B)$ and $Z_{OFF}=1+q_A+q_B+\omega q_A q_B$;

wherein when the selected logic function is OR, $Z_{ON}=q_o(1+\omega q_A+\omega q_B+2\omega q_A q_B)$ and $Z_{OFF}=1+q_A+q_B+q_A q_B$;

wherein when the selected logic function is XOR, $Z_{ON}=q_o(1+\omega q_A+\omega q_B+2\omega q_A q_B)$ and $Z_{OFF}=(1+q_A+q_B+q_A q_B)\times(1+q_A+q_B+\omega q_A q_B)$; and wherein when the selected logic function is NAND, $Z_{ON}=q_o$ and $Z_{OFF}=1+q_A+q_B+\omega q_A q_B$;

where $q_o$ is the Boltzmann weight for promoter occupancy, $q_A$ and $q_B$ are ratios of the regulatory protein concentrations to the binding thresholds for input A and input B, respectively, and w is the mutual cooperativity factor.

36. The method of claim 35, wherein the cis-regulatory sequence comprises an operator sequence and a promoter sequence, and wherein protein-DNA binding affinity is programmed by selecting the operator sequence while interactions between the two or more transcription factors are programmed by selecting the position of the promoter sequence within the binding site.

* * * * *